US008673903B2

(12) United States Patent
Hübsch et al.

(10) Patent No.: US 8,673,903 B2
(45) Date of Patent: Mar. 18, 2014

(54) SUBSTITUTED 8-ALKOXY-2-AMINOTETRALIN DERIVATIVES, AND USE THEREOF

(75) Inventors: Walter Hübsch, Wuppertal (DE); Michael Hahn, Langenfeld (DE); Alexandros Vakalopoulos, Hilden (DE); Volkhart Min-Jian Li, Velbert (DE); Frank Wunder, Wuppertal (DE); Johannes-Peter Stasch, Solingen (DE); Karl-Heinz Schlemmer, Wuppertal (DE); Friederike Stoll, Düsseldorf (DE); Niels Lindner, Wuppertal (DE)

(73) Assignee: Bayer Intellectual Property GmbH, Monheim (DE)

( * ) Notice: Subject to any disclaimer, the term of this patent is extended or adjusted under 35 U.S.C. 154(b) by 0 days.

(21) Appl. No.: 13/697,342

(22) PCT Filed: May 9, 2011

(86) PCT No.: PCT/EP2011/057390
§ 371 (c)(1),
(2), (4) Date: Jan. 7, 2013

(87) PCT Pub. No.: WO2011/141409
PCT Pub. Date: Nov. 17, 2011

(65) Prior Publication Data
US 2013/0203751 A1    Aug. 8, 2013

(30) Foreign Application Priority Data
May 14, 2010   (DE) .......................... 10 2010 020 553

(51) Int. Cl.
| | |
|---|---|
| *C07C 229/38* | (2006.01) |
| *C07D 263/22* | (2006.01) |
| *C07D 265/32* | (2006.01) |
| *C07D 271/06* | (2006.01) |
| *A61K 45/06* | (2006.01) |
| *A61K 31/4015* | (2006.01) |
| *A61K 31/421* | (2006.01) |
| *A61K 31/5375* | (2006.01) |
| *A61K 31/4245* | (2006.01) |
| *A61K 31/4402* | (2006.01) |
| *C07D 207/27* | (2006.01) |
| *A61K 31/197* | (2006.01) |
| *C07D 213/30* | (2006.01) |

(52) U.S. Cl.
USPC ........ 514/230.8; 514/357; 514/364; 514/376; 514/424; 514/567; 544/165; 546/335; 548/131; 548/231; 548/551; 562/452

(58) Field of Classification Search
None
See application file for complete search history.

(56) References Cited

U.S. PATENT DOCUMENTS

| | | | |
|---|---|---|---|
| 4,873,262 | A | 10/1989 | Junge et al. |
| 4,880,802 | A | 11/1989 | Schohe et al. |
| 6,743,798 | B1 | 6/2004 | Straub et al. |
| 6,833,364 | B1 | 12/2004 | Straub et al. |
| 7,087,644 | B1 | 8/2006 | Alonso-Alija et al. |
| 2002/0173514 | A1 | 11/2002 | Stasch et al. |
| 2004/0082658 | A1 | 4/2004 | Harter et al. |
| 2004/0082798 | A1 | 4/2004 | Alonso-Alija et al. |
| 2004/0092593 | A1 | 5/2004 | Harter et al. |
| 2004/0110840 | A1 | 6/2004 | Harter et al. |
| 2004/0176446 | A1 | 9/2004 | Alonso-Alija et al. |
| 2006/0052397 | A1 | 3/2006 | Alonso-Alija et al. |

FOREIGN PATENT DOCUMENTS

| | | |
|---|---|---|
| EP | 0041488 A1 | 12/1981 |
| EP | 0064964 B1 | 11/1982 |
| EP | 0270947 B1 | 11/1987 |
| EP | 0272534 A2 | 6/1988 |
| WO | 90/15047 A1 | 12/1990 |
| WO | 99/62505 A2 | 12/1999 |
| WO | 00/06568 A1 | 2/2000 |
| WO | 00/06569 A1 | 2/2000 |
| WO | 01/19780 A2 | 3/2001 |
| WO | 02/42301 A1 | 5/2002 |
| WO | 02/070459 A1 | 9/2002 |
| WO | 02/070460 A1 | 9/2002 |
| WO | 02/070461 A1 | 9/2002 |
| WO | 02/070462 A1 | 9/2002 |
| WO | 02/070510 A2 | 9/2002 |
| WO | 03/095451 A1 | 11/2003 |
| WO | 2005/012291 A1 | 2/2005 |

OTHER PUBLICATIONS

Nossaman et al., Critical Care Research and Practice, 2012, 290805, 1-12.*
Schmidt et al., Handbook of Experimental Pharmacology, 2009, 191, 309-339.*
Evgenov et al., Nature Review Drug Discovery, 2006, 5, 755-768.*
Shafer, S., Kolkhof, P. Failure is an option: learning from unsuccessful proof-of-concept trials. Drug Discovery Today. Nov. 2008, 13, 913-916.*

(Continued)

*Primary Examiner* — Michael Barker
*Assistant Examiner* — Po-Chih Chen
(74) *Attorney, Agent, or Firm* — Karen B. King

(57) ABSTRACT

The present application relates to novel substituted 8-alkoxy-2-aminotetraline derivatives, to processes for their preparation, to their use for the treatment and/or prevention of diseases and to their use for preparing medicaments for the treatment and/or prevention of diseases, in particular for the treatment and/or prevention of cardiovascular disorders.

7 Claims, No Drawings

(56) References Cited

OTHER PUBLICATIONS

Horig, H., Pullman, W. From bench to clinic and back: Perspective on the 1st IQPC Translational Research conference. Journal of Translational Medicine. Dec. 2004, 2, 44.*

Stasch, et al.:"NO-and Haem-independent Activation of Soluble Guanylyl Cyclase: Molecular Basis and Cardiovascular Implications of a New Pharmacological Principle," British Journal of Pharmacology, 2002, 136:773-783.

Stasch, et al.: "Targeting the Heme-Oxidized Nitric Oxide Receptor for Selective Vasodilation of Diseased Blood Vessels," J. Clin. Invest., Sep. 2006, 116(9): 2552-2561.

Ghosh et al., "Studies on Oxygen Heterocycles: Part-1: Acid Catalyzed Photochemical Reactions of Some Aryldiazoketones," Tetrahedron, 1989, 4(5):1441-1446.

Liu, et al., "(R)- and (S)-5,6,7,8-Tetrahydro-l-hydroxy-N,N-dipropyl-9H-benzocyclo-hepten-8-ylamine; Stereoselective Interactions with 5-HT1A Receptors in the Brain," J. Med. Chem. 1989, 32(10):2311-2318.

Wunder et al., "A cell-based cGMP assay useful for ultra-high-throughput screening and identification of modulators of the nitric oxide/cGMP pathway," Anal. Biochem 2005, 339:104-112.

Hönicka et al., "Purified soluble guanylyl cyclase expressed in a abaculovirus/Sf9 system: stimulation by YC-1, nitric oxide, and carbon monoxide," J. Mol. Med. 1999, Bd. 77, 14-23.

McElroy, "The Preparation and Properties of Crystalline Firefly Luciferin," Arch. Biochem. Biophys, 1957, 72:358-368.

* cited by examiner

SUBSTITUTED 8-ALKOXY-2-AMINOTETRALIN DERIVATIVES, AND USE THEREOF

The present application relates to novel substituted 8-alkoxy-2-aminotetraline derivatives, to processes for their preparation, to their use for the treatment and/or prevention of diseases and to their use for preparing medicaments for the treatment and/or prevention of diseases, in particular for the treatment and/or prevention of cardiovascular disorders.

One of the most important cellular transmission systems in mammalian cells is cyclic guanosine monophosphate (cGMP). Together with nitric oxide (NO), which is released from the endothelium and transmits hormonal and mechanical signals, it forms the NO/cGMP system. Guanylate cyclases catalyze the biosynthesis of cGMP from guanosine triphosphate (GTP). The representatives of this family disclosed to date can be divided both according to structural features and according to the type of ligands into two groups: the particulate guanylate cyclases which can be stimulated by natriuretic peptides, and the soluble guanylate cyclases which can be stimulated by NO. The soluble guanylate cyclases consist of two subunits and very probably contain one heme per heterodimer, which is part of the regulatory site. The latter is of central importance for the mechanism of activation. NO is able to bind to the iron atom of heme and thus markedly increase the activity of the enzyme. Heme-free preparations cannot, by contrast, be stimulated by NO. Carbon monoxide (CO) is also able to attach to the central iron atom of heme, but the stimulation by CO is distinctly less than that by NO.

Through the production of cGMP and the regulation, resulting therefrom, of phosphodiesterases, ion channels and protein kinases, guanylate cyclase plays a crucial part in various physiological processes, in particular in the relaxation and proliferation of smooth muscle cells, in platelet aggregation and adhesion and in neuronal signal transmission, and in disorders caused by an impairment of the aforementioned processes. Under pathophysiological conditions, the NO/cGMP system may be suppressed, which may lead for example to high blood pressure, platelet activation, increased cellular proliferation, endothelial dysfunction, atherosclerosis, angina pectoris, heart failure, thromboses, stroke and myocardial infarction.

A possible way of treating such disorders which is independent of NO and aims at influencing the cGMP signaling pathway in organisms is a promising approach because of the high efficiency and few side effects which are to be expected.

Compounds, such as organic nitrates, whose effect is based on NO have to date been exclusively used for the therapeutic stimulation of soluble guanylate cyclase. NO is produced by bioconversion and activates soluble guanylate cyclase by attaching to the central iron atom of heme. Besides the side effects, the development of tolerance is one of the crucial disadvantages of this mode of treatment [O. V. Evgenov et al., Nature Rev. Drug Disc. 5 (2006), 755].

Substances which directly stimulate soluble guanylate cyclase, i.e. without previous release of NO, have been identified in recent years. The indazole derivative YC-1 was the first NO-independent but heme-dependent sGC stimulator described [Evgenov et al., ibid.]. Based on YC-1, further substances were discovered which are more potent than YC-1 and show no relevant inhibition of phosphodiesterases (PDE). This led to the identification of the pyrazolopyridine derivatives BAY 41-2272, BAY 41-8543 and BAY 63-2521. Together with the recently published structurally different substances CMF-1571 and A-350619, these compounds form the new class of the sGC stimulators [Evgenov et al., ibid.]. A common characteristic of this substance class is an NO-independent and selective activation of the heme-containing sGC. In addition, the sGC stimulators in combination with NO have a synergistic effect on sGC activation based on a stabilization of the nitrosyl-heme complex. The exact binding site of the sGC stimulators at the sGC is still being debated. If the heme group is removed from the soluble guanylate cyclase, the enzyme still has a detectable catalytic basal activity, i.e. cGMP is still being formed. The remaining catalytic basal activity of the heme-free enzyme cannot be stimulated by any of the stimulators mentioned above [Evgenov et al., ibid.].

In addition, NO— and heme-independent sGC activators, with BAY 58-2667 as prototype of this class, have been identified. Common characteristics of these substances are that in combination with NO they only have an additive effect on enzyme activation, and that the activation of the oxidized or heme-free enzyme is markedly higher than that of the heme-containing enzyme [Evgenov et al., ibid.; J. P. Stasch et al., Br. J. Pharmacol. 136 (2002), 773; J. P. Stasch et al., J. Clin. Invest. 116 (2006), 2552]. Spectroscopic studies show that BAY 58-2667 displaces the oxidized heme group which, as a result of the weakening of the iron-histidine bond, is attached only weakly to the sGC. It has also been shown that the characteristic sGC heme binding motif Tyr-x-Ser-x-Arg is absolutely essential both for the interaction of the negatively charged propionic acids of the heme group and for the action of BAY 58-2667. Against this background, it is assumed that the binding site of BAY 58-2667 at the sGC is identical to the binding site of the heme group [J. P. Stasch et al., J. Clin. Invest. 116 (2006), 2552].

It was an object of the present invention to provide novel compounds which act as NO— and heme-independent activators of soluble guanylate cyclase in the manner described above and can be used as such in particular for the treatment and prevention of cardiovascular disorders.

Various aminodicarboxylic acid derivatives for the treatment of cardiovascular disorders have previously been described in WO 01/19780-A2, WO 02/070459-A1, WO 02/070460-A1, WO 02/070461-A1, WO 02/070462-A1 and WO 02/070510-A2. 2-Aminotetraline derivatives which can be used therapeutically in particular for CNS disorders are known from EP 0 041 488-A1, EP 0 064 964-A1, EP 0 270 947-A2, EP 0 272 534-A2, WO 90/15047-A1, FR 2 659 853-A1, WO 99/62505-A2 and WO 2005/012291-A1.

The present invention now provides a compound of the general formula (I)

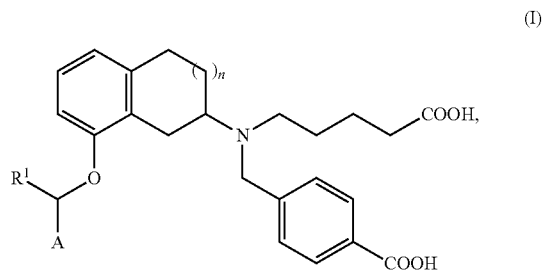

in which n represents the number 0, 1 or 2, $R^1$ represents hydrogen or methyl and
A represents a group of the formula

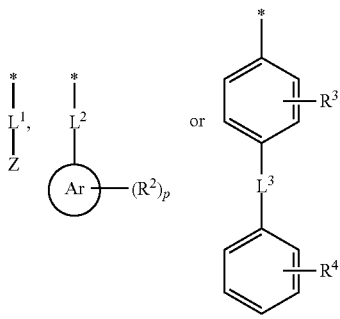

in which
* denotes the respective point of attachment to the remainder of the molecule,
$L^1$ represents straight-chain ($C_1$-$C_5$)-alkanediyl which may be mono- or disubstituted by methyl and mono- or disubstituted by fluorine,
Z represents hydrogen, fluorine, cyano, trifluoromethyl or a group of the formula

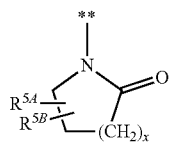

in which
** denotes the point of attachment to group $L^1$,
x represents the number 1, 2 or 3, where one of these $CH_2$ groups may be replaced by —O—,
and
$R^{5A}$ and $R^{5B}$ independently of one another represent hydrogen or methyl,
$L^2$ represents a bond or straight-chain ($C_1$-$C_5$)-alkanediyl,
Ar represents phenyl or 5- or 6-membered heteroaryl having up to three ring heteroatoms from the group consisting of N, O and S,
$R^2$ represents a substituent selected from the group consisting of fluorine, chlorine, bromine, cyano, ($C_1$-$C_4$)-alkyl, trifluoromethyl, ($C_1$-$C_4$)-alkoxy and trifluoromethoxy,
P represents the number 0, 1 or 2,
where, if the substituent $R^2$ occurs twice, its individual meanings may be identical or different,
$L^3$ represents a bond, —O—, —$CH_2$—, —$CH_2$—$CH_2$— or —CH=CH—
and
$R^3$ and $R^4$ independently of one another represent hydrogen or a substituent selected from the group consisting of fluorine, chlorine, bromine, cyano, ($C_1$-$C_4$)-alkyl, trifluoromethyl, ($C_1$-$C_4$)-alkoxy and trifluoromethoxy,
and the salts, solvates and solvates of the salts thereof.

Compounds according to the invention are the compounds of the formula (I) and their salts, solvates and solvates of the salts, the compounds included in the formula (I) of the formulae mentioned in the following and their salts, solvates and solvates of the salts, and the compounds included in the formula (I) and mentioned in the following as embodiment examples and their salts, solvates and solvates of the salts, where the compounds included in the formula (I) and mentioned in the following are not already salts, solvates and solvates of the salts.

Depending on their structure, the compounds according to the invention may exist in different stereoisomeric forms, i.e. in the form of configurational isomers or if appropriate also as conformational isomers (enantiomers and/or diastereomers, including those in the case of atropisomers). The present invention therefore encompasses the enantiomers and diastereomers and the respective mixtures thereof. The stereoisomerically uniform constituents can be isolated from such mixtures of enantiomers and/or diastereomers in a known manner; chromatography processes are preferably used for this, in particular HPLC chromatography on an achiral or chiral phase.

Where the compounds according to the invention can occur in tautomeric forms, the present invention includes all the tautomeric forms.

Preferred salts in the context of the present invention are physiologically acceptable salts of the compounds according to the invention. Salts which are not themselves suitable for pharmaceutical uses but can be used, for example, for isolation or purification of the compounds according to the invention are also included.

Physiologically acceptable salts of the compounds according to the invention include acid addition salts of conventional mineral acids, carboxylic acids and sulfonic acids, e.g. salts of hydrochloric acid, hydrobromic acid, sulfuric acid, phosphoric acid, methanesulfonic acid, ethanesulfonic acid, benzenesulfonic acid, toluenesulfonic acid, naphthalenedisulfonic acid, acetic acid, trifluoroacetic acid, propionic acid, lactic acid, tartaric acid, malic acid, citric acid, fumaric acid, maleic acid, and benzoic acid.

Physiologically acceptable salts of the compounds according to the invention also include salts of conventional bases, such as, by way of example and preferably, alkali metal salts (e.g. sodium and potassium salts), alkaline earth metal salts (e.g. calcium and magnesium salts) and ammonium salts derived from ammonia or organic amines having 1 to 16 C atoms, such as, by way of example and preferably, ethylamine, diethylamine, triethylamine, ethyldiisopropylamine, monoethanolamine, diethanolamine, triethanolamine, dicyclohexylamine, dimethylaminoethanol, procaine, dibenzylamine, N-methylpiperidine, N-methylmorpholine, lysine, arginine and 1,2-ethylenediamine.

Solvates in the context of the invention are designated as those forms of the compounds according to the invention which form a complex in the solid or liquid state by coordination with solvent molecules. Hydrates are a specific form of solvates, in which the coordination takes place with water. Hydrates are preferred solvates in the context of the present invention.

The present invention moreover also includes prodrugs of the compounds according to the invention. The term "prodrugs" here designates compounds which themselves can be biologically active or inactive, but are converted (for example metabolically or hydrolytically) into compounds according to the invention during their dwell time in the body.

The present invention comprises in particular hydrolyzable ester derivatives of the carboxylic acids of the formula (I) according to the invention. These are to be understood as meaning esters which can be hydrolyzed to the free carboxylic acids, as the compounds that are mainly active biologically, in physiological media, under the conditions of the biological tests described later and in particular in vivo by enzymatic or chemical routes. ($C_1$-$C_4$)-alkyl esters, in which the alkyl group can be straight-chain or branched, are preferred as such esters. Particular preference is given to methyl, ethyl or tert-butyl esters.

In the context of the present invention, the substituents have the following meaning, unless specified otherwise:

$(C_1-C_4)$-Alkyl in the context of the invention represents a straight-chain or branched alkyl radical having 1 to 4 carbon atoms. The following may be mentioned by way of example and by way of preference: methyl, ethyl, n-propyl, isopropyl, n-butyl, isobutyl, sec-butyl and tert-butyl.

$(C_1-C_5)$-Alkanediyl and $(C_2-C_4)$-alkanediyl in the context of the invention represent a straight-chain α,ω-divalent alkyl radical having 1 to 5 and 2 to 4 carbon atoms, respectively. The following may be mentioned by way of example and by way of preference: methylene, ethane-1,2-diyl (1,2-ethylene), propane-1,3-diyl (1,3-propylene), butane-1,4-diyl (1,4-butylene) and pentane-1,5-diyl (1,5-pentylene).

$(C_1-C_4)$-Alkoxy in the context of the invention represents a straight-chain or branched alkoxy radical having 1 to 4 carbon atoms. The following may be mentioned by way of example and by way of preference: methoxy, ethoxy, n-propoxy, isopropoxy, n-butoxy, isobutoxy, sec-butoxy and tert-butoxy.

5- or 6-membered heteroaryl in the context of the invention represents an aromatic heterocycle (heteroaromatic) having a total of 5 or 6 ring atoms which contains up to three identical or different ring heteroatoms from the group consisting of N, O and S and is attached via a ring carbon atom or optionally via a ring nitrogen atom. The following may be mentioned by way of example and by way of preference: furyl, pyrrolyl, thienyl, pyrazolyl, imidazolyl, 1,2-oxazolyl(isoxazolyl), 1,3-oxazolyl, 1,2-thiazolyl(isothiazolyl), 1,3-thiazolyl, 1,2,3-triazolyl, 1,2,4-triazolyl, 1,2,4-oxadiazolyl, 1,3,4-oxadiazolyl, 1,2,4-thiadiazolyl, 1,3,4-thiadiazolyl, pyridyl, pyrimidinyl, pyridazinyl, pyrazinyl, 1,2,4-triazinyl and 1,3,5-triazinyl.

In the context of the present invention, all radicals which occur more than once are defined independently of one another. If radicals in the compounds according to the invention are substituted, the radicals may be mono- or polysubstituted, unless specified otherwise. Substitution by one or two identical or different substituents is preferred. Particular preference is given to substitution by one substituent.

A particular embodiment of the present invention comprises compounds of the formula (I) in which
n represents the number 1
and
A and $R^1$ each have the meanings given above,
and the salts, solvates and solvates of the salts thereof.

Preference in the context of the present invention is given to compounds of the formula (I) in which
n represents the number 1,
$R^1$ represents hydrogen
and
A represents a group of the formula

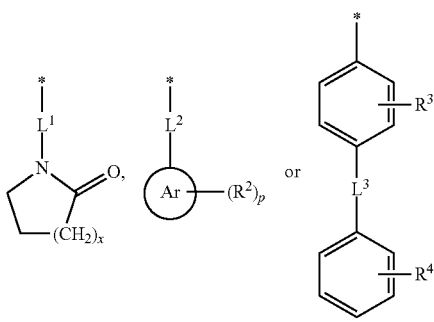

in which
* denotes the respective point of attachment to the remainder of the molecule,
$L^1$ represents straight-chain $(C_2-C_4)$-alkanediyl,
x represents the number 1 or 2, where one of these $CH_2$ groups may be replaced by —O—,
$L^2$ represents a bond or —$CH_2$—,
Ar represents phenyl, pyridyl, 1,2,4-oxadiazolyl or 1,3,4-oxadiazolyl,
$R^2$ represents a substituent selected from the group consisting of fluorine, chlorine, $(C_1-C_4)$-alkyl and trifluoromethyl,
P represents the number 0 or 1,
$L^3$ represents a bond or —$CH_2$—$CH_2$
and
$R^3$ and $R^4$ independently of one another represent hydrogen or a substituent selected from the group consisting of fluorine, chlorine, $(C_1-C_4)$-alkyl and trifluoromethyl,
and the salts, solvates and solvates of the salts thereof.

Particular preference in the context of the present invention is given to compounds of the formula (I) in which
n represents the number 1,
$R^1$ represents hydrogen
and
A represents a group of the formula

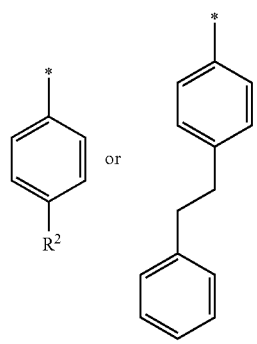

in which
* denotes the respective point of attachment to the remainder of the molecule
and
$R^2$ represents methyl, ethyl, isopropyl or tert-butyl,
and the salts, solvates and solvates of the salts thereof.

The definitions of radicals indicated specifically in the respective combinations or preferred combinations of radicals are replaced as desired irrespective of the particular combinations indicated for the radicals also by definitions of radicals of other combinations.

Combinations of two or more of the abovementioned preferred ranges are very particularly preferred.

The invention furthermore provides a process for preparing the compounds of the formula (I) according to the invention, characterized in that a compound of the formula (II)

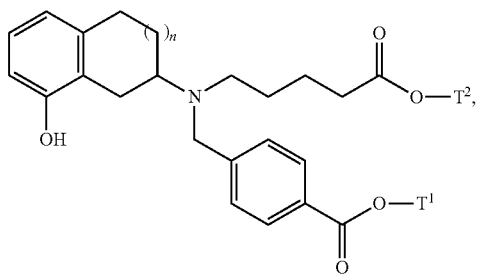

(II)

in which n has the meaning given above
and
$T^1$ and $T^2$ are identical or different and represent $(C_1-C_4)$-alkyl
are reacted in the presence of a base with a compound of the formula (III)

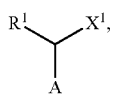

(III)

in which $R^1$ and A have the meanings given above
and
X' represents a leaving group such as, for example, chlorine, bromine, iodine, mesylate, triflate or tosylate,
to give a compound of the formula (IV)

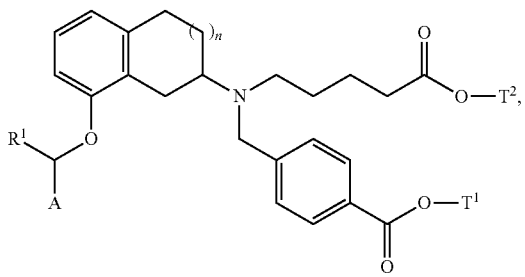

(IV)

in which n, $R^1$, A, $T^1$ and $T^2$ each have the meanings given above,
and this is then converted by hydrolysis of the ester groupings —C(O)OT$^1$ and —C(O)OT into the corresponding dicarboxylic acid of the formula (I)
and the compounds of the formula (I) obtained in this manner are separated where appropriate into their enantiomers and/or diastereomers, and/or where appropriate reacted with the appropriate (i) solvents and/or (ii) bases or acids to give the solvates, salts and/or solvates of the salts thereof.

Suitable inert solvents for process step (II)+(III)→(IV) are, for example, ethers such as diethyl ether, diisopropyl ether, methyl tert-butyl ether, tetrahydrofuran, 1,4-dioxane, 1,2-dimethoxyethane or bis-(2-methoxyethyl)ether, hydrocarbons such as benzene, toluene, xylene, pentane, hexane, heptane, cyclohexane or mineral oil fractions, or dipolar aprotic solvents such as acetone, methyl ethyl ketone, acetonitrile, N,N-dimethylformamide (DMF), N,N-dimethylacetamide (DMA), dimethyl sulfoxide (DMSO), N,N'-dimethylpropyleneurea (DMPU) or N-methylpyrrolidinone (NMP). It is also possible to use mixtures of such solvents. Preference is given to using acetonitrile or dimethylformamide Suitable bases for process step (II)+(III)→(IV) are in particular alkali metal carbonates such as sodium carbonate, potassium carbonate or cesium carbonate, alkali metal alkoxides such as sodium methoxide or potassium methoxide, sodium ethoxide or potassium ethoxide or sodium tert-butoxide or potassium tert-butoxide, alkali metal hydrides such as sodium hydride or potassium hydride, amides such as sodium amide, lithium bis(trimethylsilyl)amide or potassium bis(trimethyl-silyl)amide or lithium diisopropylamide, or organometallic compounds such as n-butyllithium or phenyllithium. Preferably, the base employed is sodium carbonate, potassium carbonate or cesium carbonate. If appropriate, the addition of an alkylating catalyst such as, for example, lithiumbromid, sodium iodide or potassium iodide, tetra-n-butylammonium bromide or benzyltriethyl-ammonium chloride is advantageous.

The reaction (II)+(III)→(IV) is generally carried out in a temperature range of from 0° C. to +150° C., preferably at from +20° C. to +100° C.

The hydrolysis of the ester groups —C(O)OT$^1$ and —C(O)OT in process step (IV)→(I) is carried out by customary methods by treating the esters in inert solvents with acids or bases, where in the latter variant the salts initially formed are converted by treatment with acid into the free carboxylic acids. In the case of the tert-butyl esters, the ester cleavage is preferably carried out using acids.

In the case of different groups T$^1$ and T$^2$, the hydrolysis can optionally be carried out simultaneously in a one-pot reaction or in two separate reaction steps.

Suitable inert solvents for these reactions are water or the organic solvents customary for an ester cleavage. These preferably include alcohols such as methanol, ethanol, n-propanol, isopropanol, n-butanol or tert-butanol, or ethers such as diethyl ether, tetrahydrofuran, 1,4-dioxane or 1,2-dimethoxyethane, or other solvents such as dichloromethane, acetone, methyl ethyl ketone, N,N-dimethylformamide or dimethyl sulfoxide. It is also possible to use mixtures of these solvents. In the case of a basic ester hydrolysis, preference is given to using mixtures of water with dioxane, tetrahydrofuran, methanol, ethanol and/or dimethylformamide. In the case of a reaction with trifluoroacetic acid, preference is given to using dichloromethane, and in the case of a reaction with hydrogen chloride, preference is given to using tetrahydrofuran, diethyl ether, dioxane or water.

Suitable bases are the customary inorganic bases. These include in particular alkali metal or alkaline earth metal hydroxides such as, for example, lithium hydroxide, sodium hydroxide, potassium hydroxide or barium hydroxide, or alkali metal or alkaline earth metal carbonates such as sodium carbonate, potassium carbonate or calcium carbonate. Preference is given to using lithium hydroxide, sodium hydroxide or potassium hydroxide.

Suitable acids for the ester cleavage are, in general, sulfuric acid, hydrogen chloride/hydrochloric acid, hydrogen bromide/hydrobromic acid, phosphoric acid, acetic acid, trifluoroacetic acid, toluenesulfonic acid, methansulfonic acid or trifluoromethanesulfonic acid or mixtures thereof, if appropriate with the addition of water. Preference is given to hydrogen chloride or trifluoroacetic acid in the case of the tert-butyl esters and hydrochloric acid in the case of the methyl esters.

The ester cleavage is generally carried out in a temperature range of from −20° C. to +120° C., preferably at from 0° C. to +80° C.

The process steps described above can be carried out at atmospheric pressure, at elevated pressure or at reduced pressure (for example in the range from 0.5 to 5 bar); in general, the reactions are in each case carried out under atmospheric pressure.

For their part, the compounds of the formula (II) can be prepared, for example, by initially converting a keto compound of the formula (V)

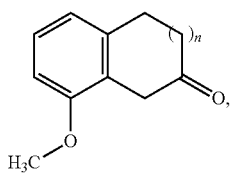

(V)

in which n has the meaning given above, in the course of a reductive amination with a 4-(aminomethyl) benzoic ester of the formula (VI)

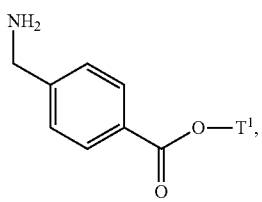

(VI)

in which $T^1$ has the meaning given above, into a secondary amine of the formula (VII)

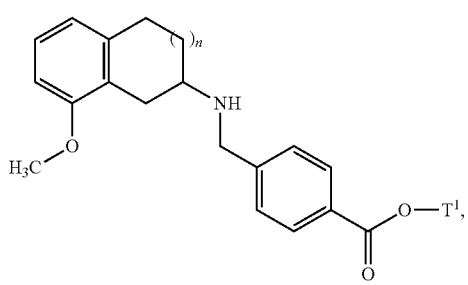

(VII)

in which n and $T^1$ have the meanings given above, then alkylating in the presence of a base with a 5-halovaleric ester of the formula (VIII)

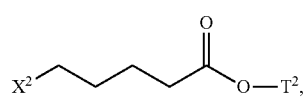

(VIII)

in which $T^2$ has the meaning given above and $X^2$ represents chlorine, bromine or iodine, to give a tertiary amine of the formula (IX)

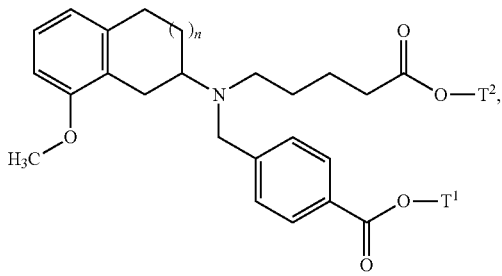

(IX)

in which n, $T^1$ and $T^2$ each have the meanings given above, and then cleaving the phenolic methyl ether grouping by treatment with boron tribromide or hydrogen bromide.

The reaction (V)+(VI)→(VII) is carried out in the solvents which are customary for a reductive amination and inert under the reaction conditions, if appropriate in the presence of an acid and/or a dehydrating agent as catalysts. These solvents include, for example, water, tetrahydrofuran, dichloromethane, 1,2-dichloroethane, N,N-dimethylformamide and alcohols such as methanol, ethanol, n-propanol or isopropanol; it is also possible to use mixtures of such solvents. Preference is given to using dichloromethane, methanol or ethanol, in each case with addition of acetic acid.

Suitable reducing agents for such an amination reaction are in particular complex borohydrides such as, for example, sodium borohydride, sodium triacetoxyborohydride, sodium cyanoboro-hydride or tetra-n-butylammonium borohydride. Preference is given to using sodium borohydride or sodium triacetoxyborohydride.

The reaction (V)+(VI)→(VII) is generally carried out in a temperature range of from −20° C. to +50° C., preferably at from 0° C. to +30° C.

The alkylation in process step (VII)+(VIII)→(IX) is carried out under analogous reaction conditions with respect to solvent, base and temperature, as described above for the reaction (II)+(III)→(IV). Here, the bases and solvents used are preferably alkali metal carbonates and acetonitrile, respectively. The alkylation is generally carried out in a temperature range of from +50° C. to +85° C.

The cleavage of the phenolic methyl ether group in process step (IX)→(II) is carried out according to customary methods by treatment with boron tribromide in dichloromethane at from −20° C. to +10° C. or by heating with a solution of hydrogen bromide in glacial acetic acid or water to from +100° C. to +120° C. If all or some of the ester groupings —C(O)OT¹ and —C(O)OT² are also cleaved at the same time under the reaction conditions giving the corresponding free carboxylic acids of the formula (X)

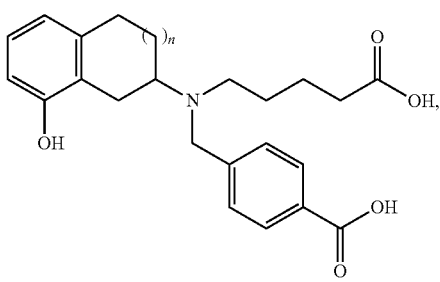

(X)

in which n has the meaning given above, these can be re-esterified again for example by subsequent treatment with thionyl chloride in methanol or ethanol.

The reactions described above can be carried out at atmospheric pressure, at elevated pressure or at reduced pressure (for example in the range from 0.5 to 5 bar); in general, the reactions are in each case carried out under atmospheric pressure.

A separation of the compounds according to the invention into the corresponding enantiomers and/or diastereomers can optionally, if expedient, also take place as early as at the stage of the compounds (II), (IV), (VII), (IX) or (X) which are then reacted further in separated form in a manner corresponding to the process sequences described above. Such a separation of the stereo-isomers can be carried out by customary methods known to the person skilled in the art. Preference is given to using chromatographic methods on achiral or chiral separation phases; if the intermediates or end products are carboxylic acids, separation may alternatively also be via diastereomeric salts with the aid of chiral bases.

The compounds of the formula (V) can in each case be obtained by literature procedures [see, for example, S. Ghosh et al., *Tetrahedron* 1989, 45 (5), 1441-1446 for 4-methoxy-1,3-dihydro-2H-inden-2-one (n=0); N. T. Hatzenbuhler et al., WO 2005/012291-A1, Example 45 for 8-methoxy-3,4-dihydronaphthalen-2(1H)-one (n=1); U. Hacksell et al., *J. Med. Chem.* 1989, 32 (10), 2311-2318 for 4-methoxy-5,7,8,9-tetrahydro-6H-benzo[7]annulen-6-one (n=2)].

The compounds of the formulae (III), (VI) and (VIII) are either commercially available or described as such in the literature, or they can be prepared by routes obvious to the person skilled in the art analogously to methods published in the literature. Numerous detailed procedures can also be found in the experimental part in the section on the preparation of the starting materials and intermediates.

The preparation of the compounds according to the invention can be illustrated in an exemplary manner by the reaction scheme below:

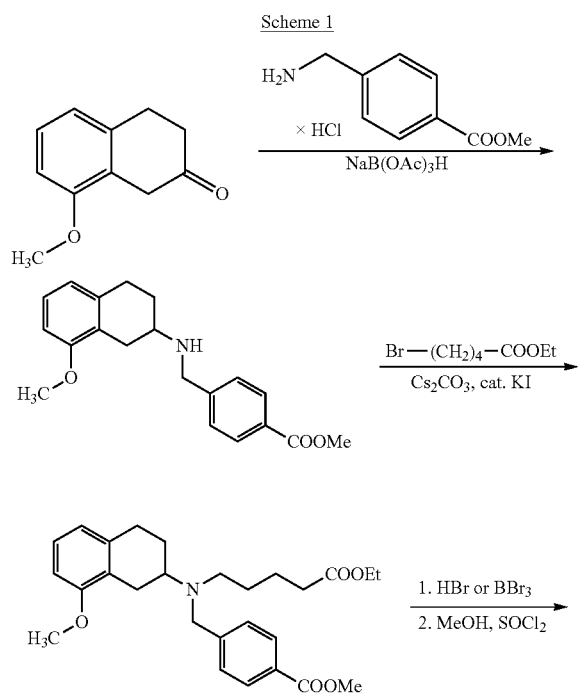

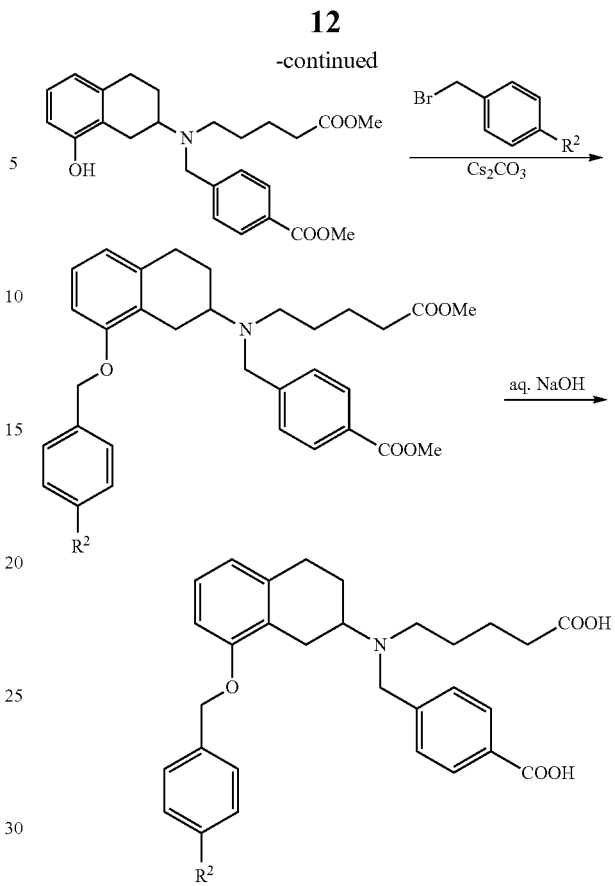

The compounds according to the invention have valuable pharmacological properties and can be used for the prevention and treatment of disorders in humans and animals.

The compounds according to the invention are potent activators of soluble guanylate cyclase. They lead to vasorelaxation, inhibition of platelet aggregation and lowering of blood pressure and increase of coronary blood flow. These effects are mediated via direct heme-independent activation of soluble guanylate cyclase and an increase of intracellular cGMP.

The compounds according to the invention can therefore be employed in medicaments for the treatment of cardiovascular disorders such as, for example, for the treatment of high blood pressure and heart failure, stable and unstable angina pectoris, pulmonary hypertension, renal hypertension, peripheral and cardiac vascular disorders, arrhythmias, for the treatment of thromboembolic disorders and ischemias such as myocardial infarction, stroke, transistory and ischemic attacks, disturbances of peripheral blood flow, for the prevention of restenoses as after thrombolysis therapies, percutaneous transluminal angioplasties (PTAs), percutaneous transluminal coronary angioplasties (PTCAs) and bypass, and for the treatment of arteriosclerosis, asthmatic disorders and diseases of the urogenital system such as, for example, an overactive bladder, lower urinary tract symptoms (LUTS), incontinence, prostate hypertrophy, erectile dysfunction, female sexual dysfunction, and for treating osteoporosis, glaucoma, and gastroparesis.

The compounds according to the invention can additionally be used for the treatment of primary and secondary Raynaud's phenomenon, of microcirculation impairments, claudication, tinnitus, peripheral and autonomic neuropathies, diabetic microangiopathies, diabetic retinopathy, diabetic ulcers on the extremities, CREST syndrome, erythematosis, onychomycosis and rheumatic disorders.

In addition, the compounds according to the invention can be used for preventing ischemia- and/or reperfusion-related damage to organs or tissues and also as additives for perfusion and preservation solutions of organs, organ parts, tissues or tissue parts of human or animal origin in particular for surgical interventions or in the field of transplantation medicine.

The compounds according to the invention are furthermore suitable for the treatment of respiratory distress syndromes and chronic obstructive airway disorders (COPD), of acute and chronic renal failure and for promoting wound healing.

The compounds described in the present invention also represent active ingredients for controlling central nervous system diseases characterized by disturbances of the NO/cGMP system. They are suitable in particular for improving perception, concentration, learning or memory after cognitive impairments like those occurring in particular in association with situations/diseases/syndromes such as mild cognitive impairment, age-associated learning and memory impairments, age-associated memory loss, vascular dementia, craniocerebral trauma, stroke, dementia occurring after strokes (post-stroke dementia), post-traumatic craniocerebral trauma, general concentration impairments, concentration impairments in children with learning and memory problems, Alzheimer's disease, Lewy body dementia, dementia with degeneration of the frontal lobes including Pick's syndrome, Parkinson's disease, progressive nuclear palsy, dementia with corticobasal degeneration, amyolateral sclerosis (ALS), Huntington's disease, multiple sclerosis, thalamic degeneration, Creutzfeld-Jacob dementia, HIV dementia, schizophrenia with dementia or Korsakoff's psychosis. They are also suitable for the treatment of central nervous system disorders such as states of anxiety, tension and depression, CNS-related sexual dysfunctions and sleep disturbances, and for controlling pathological disturbances of the intake of food, stimulants and addictive substances.

The compounds according to the invention are furthermore also suitable for controlling cerebral blood flow and represent effective agents for controlling migraine. They are also suitable for the prophylaxis and control of the sequelae of cerebral infarctions (Apoplexia cerebri) such as stroke, cerebral ischemias and craniocerebral trauma. The compounds according to the invention can likewise be employed for controlling states of pain.

In addition, the compounds according to the invention have an anti-inflammatory effect and can therefore be employed as anti-inflammatory agents.

The present invention further relates to the use of the compounds according to the invention for the treatment and/or prevention of disorders, especially of the aforementioned disorders.

The present invention further relates to the use of the compounds according to the invention for producing a medicament for the treatment and/or prevention of disorders, especially of the aforementioned disorders.

The present invention further relates to the use of the compounds according to the invention in a method for the treatment and/or prevention of disorders, especially of the aforementioned disorders.

The present invention further relates to a method for the treatment and/or prevention of disorders, especially of the aforementioned disorders, by using an effective amount of at least one of the compounds according to the invention.

The compounds according to the invention can be employed alone or, if required, in combination with other active ingredients. The present invention further relates to medicaments comprising at least one of the compounds according to the invention and one or more further active ingredients, in particular for the treatment and/or prevention of the aforementioned disorders. Examples of suitable combination active ingredients which may be preferably mentioned are:

organic nitrates and NO donors such as, for example, sodium nitroprusside, nitroglycerin, isosorbide mononitrate, isosorbide dinitrate, molsidomine or SIN-1, and inhaled NO;

compounds which inhibit the breakdown of cyclic guanosine monophosphate (cGMP), such as, for example, inhibitors of phosphodiesterases (PDE) 1, 2 and/or 5, in particular PDE 5 inhibitors such as sildenafil, vardenafil and tadalafil;

NO-independent but heme-dependent stimulators of guanylate cyclase, such as, in particular, the compounds described in WO 00/06568, WO 00/06569, WO 02/42301 and WO 03/095451;

agents having antithrombotic activity, for example and preferably from the group of platelet aggregation inhibitors, of anticoagulants or of profibrinolytic substances;

active ingredients which lower blood pressure, for example and preferably from the group of calcium antagonists, angiotensin AII antagonists, ACE inhibitors, endothelin antagonists, renin inhibitors, alpha-receptor blockers, beta-receptor blockers, mineralocorticoid receptor antagonists, and of diuretics; and/or active ingredients which modify lipid metabolism, for example and preferably from the group of thyroid receptor agonists, cholesterol synthesis inhibitors such as, for example and preferably, HMG-CoA reductase inhibitors or squalene synthesis inhibitors, of ACAT inhibitors, CETP inhibitors, MTP inhibitors, PPAR-alpha, PPAR-gamma and/or PPAR-delta agonists, cholesterol absorption inhibitors, lipase inhibitors, polymeric bile acid adsorbents, bile acid reabsorption inhibitors and lipoprotein (a) antagonists.

Agents having antithrombotic activity preferably mean compounds from the group of platelet aggregation inhibitors, of anticoagulants or of profibrinolytic substances.

In a preferred embodiment of the invention, the compounds according to the invention are administered in combination with a platelet aggregation inhibitor such as, for example and preferably, aspirin, clopidogrel, ticlopidin or dipyridamole.

In a preferred embodiment of the invention, the compounds according to the invention are administered in combination with a thrombin inhibitor such as, for example and preferably, ximelagatran, melagatran, bivalirudin or clexane.

In a preferred embodiment of the invention, the compounds according to the invention are administered in combination with a GPIIb/IIIa antagonist such as, for example and preferably, tirofiban or abciximab.

In a preferred embodiment of the invention, the compounds according to the invention are administered in combination with a factor Xa inhibitor such as, for example and preferably, rivaroxaban, apixaban, fidexaban, razaxaban, fondaparinux, idraparinux, DU-176b, PMD-3112, YM-150, KFA-1982, EMD-503982, MCM-17, MLN-1021, DX 9065a, DPC 906, JTV 803, SSR-126512 or SSR-128428.

In a preferred embodiment of the invention, the compounds according to the invention are administered in combination with heparin or with a low molecular weight (LMW) heparin derivative.

In a preferred embodiment of the invention, the compounds according to the invention are administered in combination with a vitamin K antagonist such as, for example and preferably, coumarin.

Agents which lower blood pressure preferably mean compounds from the group of calcium antagonists, angiotensin AII antagonists, ACE inhibitors, endothelin antagonists, renin inhibitors, alpha-receptor blockers, beta-receptor blockers, mineralocorticoid receptor antagonists, and of diuretics.

In a preferred embodiment of the invention, the compounds according to the invention are administered in combination with a calcium antagonist such as, for example and preferably, nifedipine, amlodipine, verapamil or diltiazem.

In a preferred embodiment of the invention, the compounds according to the invention are administered in combination with an alpha-1-receptor blocker such as, for example and preferably, prazosin.

In a preferred embodiment of the invention, the compounds according to the invention are administered in combination with a beta-receptor blocker such as, for example and preferably, propranolol, atenolol, timolol, pindolol, alprenolol, oxprenolol, penbutolol, bupranolol, metipranolol, nadolol, mepindolol, carazalol, sotalol, metoprolol, betaxolol, celiprolol, bisoprolol, carteolol, esmolol, labetalol, carvedilol, adaprolol, landiolol, nebivolol, epanolol or bucindolol.

In a preferred embodiment of the invention, the compounds according to the invention are administered in combination with an angiotensin AII antagonist such as, for example and preferably, losartan, candesartan, valsartan, telmisartan or embursatan.

In a preferred embodiment of the invention, the compounds according to the invention are administered in combination with an ACE inhibitor such as, for example and preferably, enalapril, captopril, lisinopril, ramipril, delapril, fosinopril, quinopril, perindopril or trandopril.

In a preferred embodiment of the invention, the compounds according to the invention are administered in combination with an endothelin antagonist such as, for example and preferably, bosentan, darusentan, ambrisentan or sitaxsentan.

In a preferred embodiment of the invention, the compounds according to the invention are administered in combination with a renin inhibitor such as, for example and preferably, aliskiren, SPP-600 or SPP-800.

In a preferred embodiment of the invention, the compounds according to the invention are administered in combination with a mineralocorticoid receptor antagonist such as, for example and preferably, spironolactone or eplerenone.

In a preferred embodiment of the invention, the compounds according to the invention are administered in combination with a diuretic such as, for example and preferably, furosemide.

Agents which modify lipid metabolism preferably mean compounds from the group of CETP inhibitors, thyroid receptor agonists, cholesterol synthesis inhibitors such as HMG-CoA reductase inhibitors or squalene synthesis inhibitors, of ACAT inhibitors, MTP inhibitors, PPAR-alpha, PPAR-gamma and/or PPAR-delta agonists, cholesterol absorption inhibitors, polymeric bile acid adsorbents, bile acid reabsorption inhibitors, lipase inhibitors and of lipoprotein (a) antagonists.

In a preferred embodiment of the invention, the compounds according to the invention are administered in combination with a CETP inhibitor such as, for example and preferably, torcetrapib (CP-529 414), JJT-705 or CETP vaccine (Avant).

In a preferred embodiment of the invention, the compounds according to the invention are administered in combination with a thyroid receptor agonist such as, for example and preferably, D-thyroxine, 3,5,3'-triiodothyronine (T3), CGS 23425 or axitirome (CGS 26214).

In a preferred embodiment of the invention, the compounds according to the invention are administered in combination with an HMG-CoA reductase inhibitor from the class of statins such as, for example and preferably, lovastatin, simvastatin, pravastatin, fluvastatin, atorvastatin, rosuvastatin, or pitavastatin.

In a preferred embodiment of the invention, the compounds according to the invention are administered in combination with a squalene synthesis inhibitor such as, for example and preferably, BMS-188494 or TAK-475.

In a preferred embodiment of the invention, the compounds according to the invention are administered in combination with an ACAT inhibitor such as, for example and preferably, avasimibe, melinamide, pactimibe, eflucimibe or SMP-797.

In a preferred embodiment of the invention, the compounds according to the invention are administered in combination with an MTP inhibitor such as, for example and preferably, implitapide, BMS-201038, R-103757 or JTT-130.

In a preferred embodiment of the invention, the compounds according to the invention are administered in combination with a PPAR-gamma agonist such as, for example and preferably, pioglitazone or rosiglitazone.

In a preferred embodiment of the invention, the compounds according to the invention are administered in combination with a PPAR-delta agonist such as, for example and preferably, GW 501516 or BAY 68-5042.

In a preferred embodiment of the invention, the compounds according to the invention are administered in combination with a cholesterol absorption inhibitor such as, for example and preferably, ezetimibe, tiqueside or pamaqueside.

In a preferred embodiment of the invention, the compounds according to the invention are administered in combination with a lipase inhibitor such as, for example and preferably, orlistat.

In a preferred embodiment of the invention, the compounds according to the invention are administered in combination with a polymeric bile acid adsorbent such as, for example and preferably, cholestyramine, colestipol, colesolvam, Cholesta-Gel or colestimide.

In a preferred embodiment of the invention, the compounds according to the invention are administered in combination with a bile acid reabsorption inhibitor such as, for example and preferably, ASBT (=IBAT) inhibitors such as, for example, AZD-7806, S-8921, AK-105, BARI-1741, SC-435 or SC-635.

In a preferred embodiment of the invention, the compounds according to the invention are administered in combination with a lipoprotein (a) antagonist such as, for example and preferably, gemcabene calcium (CI-1027) or nicotinic acid.

The present invention further relates to medicaments which comprise at least one compound according to the invention, normally together with one or more inert, non-toxic, pharmaceutically suitable excipients, and to the use thereof for the aforementioned purposes.

The compounds according to the invention can act systemically and/or locally. For this purpose, they can be administered in a suitable way such as, for example, by the oral, parenteral, pulmonary, nasal, sublingual, lingual, buccal, rectal, dermal, transdermal, conjunctival, otic routes or as implant or stent.

The compounds according to the invention can be administered in administration forms suitable for these administration routes.

Suitable for oral administration are administration forms which function according to the prior art and deliver the compounds according to the invention rapidly and/or in modified fashion, and which contain the compounds according to the invention in crystalline and/or amorphized and/or dissolved form, such as, for example, tablets (uncoated or coated tablets, for example having enteric coatings or coatings which are insoluble or dissolve with a delay and control the release of the compound according to the invention), tablets which disintegrate rapidly in the mouth, or films/wafers, films/lyophilisates, capsules (for example hard or soft gelatin capsules), sugar-coated tablets, granules, pellets, powders, emulsions, suspensions, aerosols or solutions.

Parenteral administration can take place with avoidance of an absorption step (e.g. intravenous, intraarterial, intracardiac, intraspinal or intralumbar) or with inclusion of an absorption (e.g. intramuscular, subcutaneous, intracutaneous, percutaneous or intraperitoneal). Administration forms suitable for parenteral administration are, inter alia, preparations for injection and infusion in the form of solutions, suspensions, emulsions, lyophilisates or sterile powders.

Suitable for the other administration routes are, for example, pharmaceutical forms for inhalation (inter alia powder inhalers, nebulizers), nasal drops, solutions or spray, tablets for lingual, sublingual or buccal administration, films/wafers or capsules, suppositories, preparations for the ears or eyes, vaginal capsules, aqueous suspensions (lotions, shaking mixtures), lipophilic suspensions, ointments, creams, transdermal therapeutic systems (e.g. patches), milk, pastes, foams, dusting powders, implants or stents.

Oral or parenteral administration is preferred, especially oral and intravenous administration.

The compounds according to the invention can be converted into the stated administration forms. This can take place in a manner known per se by mixing with inert, non-toxic, pharmaceutically suitable excipients. These excipients include, inter alia, carriers (for example microcrystalline cellulose, lactose, mannitol), solvents (e.g. liquid polyethylene glycols), emulsifiers and dispersants or wetting agents (for example sodium dodecyl sulfate, polyoxysorbitan oleate), binders (for example polyvinylpyrrolidone), synthetic and natural polymers (for example albumin), stabilizers (e.g. antioxidants such as, for example, ascorbic acid), colorants (e.g. inorganic pigments such as, for example, iron oxides) and masking flavors and/or odors.

It has generally proved advantageous to administer on parenteral administration amounts of about 0.001 to 1 mg/kg, preferably about 0.01 to 0.5 mg/kg, of body weight to achieve effective results, and on oral administration the dosage is about 0.01 to 100 mg/kg, preferably about 0.01 to 20 mg/kg, and very particularly preferably 0.1 to 10 mg/kg, of body weight.

It may nevertheless be necessary where appropriate to deviate from the stated amounts, in particular as a function of the body weight, route of administration, individual response to the active ingredient, nature of the preparation and time or interval over which administration takes place. Thus, it may be sufficient in some cases to make do with less than the aforementioned minimum amount, whereas in other cases the stated upper limit must be exceeded. It may in the event of administration of larger amounts be advisable to divide these into a plurality of individual doses over the day.

The following exemplary embodiments illustrate the invention. The invention is not restricted to the examples.

The percentage data in the following tests and examples are, unless indicated otherwise, percentages by weight; parts are parts by weight. Solvent ratios, dilution ratios and concentration data for the liquid/liquid solutions are in each case based on volume.

A. EXAMPLES

Abbreviations and Acronyms abs. absolute
ac acetyl
aq. aqueous, aqueous solution
ATP adenosine 5'-triphosphate
Brij® polyethylene glycol dodecyl ether
BSA bovine serum albumin
Ex. Example
c concentration
cat. catalytic
DMF dimethylformamide
DMSO dimethyl sulfoxide
DTT dithiothreitol
ee enantiomeric excess
ent enantiomerically pure, enantiomer
eq. equivalent(s)
ESI electron impact ionization (in MS)
Et ethyl
GTP guanosine 5'-triphosphate
h hour(s)
HPLC high pressure, high performance liquid chromatography
LC-MS liquid chromatography-coupled mass spectrometry
Me methyl
min minute(s)
MS mass spectroscopy
NMR nuclear magnetic resonance spectrometry
rac racemic, racemate
RP reverse phase (in HPLC)
RT room temperature
$R_t$ retention time (in HPLC)
TEA triethanolamine
TFA trifluoroacetic acid
THF tetrahydrofuran
UV ultraviolet spectroscopy
v/v ratio by volume (of a solution)
tog. together HPLC and LC-MS Methods:

Method 1 (Preparative HPLC):

Column: Grom-Sil C18 10 µm, 250 mm×30 mm; mobile phase A: water+0.1% formic acid, mobile phase B: acetonitrile; program: 0-5 min 10% B, 5-38 min gradient up to 95% B; flow rate: 50 ml/min; UV detection: 210 nm.

Method 2 (LC-MS):

Instrument: Waters Acquity SQD UPLC System; column: Waters Acquity UPLC HSS T3 1.8µ, 50 mm×1 mm; mobile phase A: 1 l of water+0.25 ml of 99% strength formic acid, mobile phase B: 1 l of acetonitrile+0.25 ml of 99% strength formic acid; gradient: 0.0 min 90% A→1.2 min 5% A→2.0 min 5% A; flow rate: 0.40 ml/min; oven: 50° C.; UV detection: 210-400 nm.

Method 3 (LC-MS):

MS instrument type: Waters Micromass Quattro Micro; HPLC instrument type: Agilent 1100 series; column: Thermo Hypersil GOLD 3µ, 20 mm×4 mm; mobile phase A: 1 l of water+0.5 ml of 50% strength formic acid, mobile phase B: 1 l of acetonitrile+0.5 ml of 50% strength formic acid; gradient: 0.0 min 100% A→3.0 min 10% A→4.0 min 10% A→4.01 min 100% A→(flow rate 2.5 ml/min)→5.00 min 100% A; oven: 50° C.; flow rate: 2 ml/min; UV detection: 210 nm.

Method 4 (LC-MS):

Instrument: Micromass Quattro Premier with Waters UPLC Acquity; column: Thermo Hypersil GOLD 1.9μ, 50 mm×1 mm; mobile phase A: 1 l of water+0.5 ml of 50% strength formic acid, mobile phase B: 1 l of acetonitrile+0.5 ml of 50% strength formic acid; gradient 0.0 min 90% A→0.1 min 90% A→1.5 min 10% A→2.2 min 10% A; flow rate: 0.33 ml/min; oven: 50° C.; UV detection: 210 nm.

Method 5 (Chiral Analytical HPLC):

Stationary phase: Daicel OD-H; column: 250 mm×4 mm; UV detection: 230 nm; mobile phase: isopropanol/isohexane 30:70 (v/v); flow rate: 1.0 ml/min.

Method 6 (Chiral Analytical HPLC):

Stationary phase: Daicel Chiralpak IA; column: 250 mm×4 mm; UV detection: 230 nm; mobile phase: ethanol/methyl tert-butyl ether 75:25 (v/v); flow rate: 1.0 ml/min.

Method 7 (Preparative LC-MS):

MS instrument: Waters, HPLC instrument: Waters; column: Waters X-Bridge C18 5 μm, 18 mm×50 mm; mobile phase A: water+0.05% triethylamine, mobile phase B: acetonitrile+0.05% triethylamine; gradient: 0.0 min 95% A→0.15 min 95% A→8.0 min 5% A→9.0 min 5% A; flow rate: 40 ml/min; UV detection: DAD, 210-400 nm.

Method 8 (Preparative LC-MS):

MS instrument: Waters, HPLC instrument: Waters; column: Phenomenex Luna 5μ C18(2) 100A, 50 mm×21.2 mm; mobile phase A: water+0.05% formic acid, mobile phase B: acetonitrile+0.05% formic acid; gradient: 0.0 min 95% A→0.15 min 95% A→8.0 min 5% A→9.0 min 5% A; flow rate: 40 ml/min; UV detection: DAD, 210-400 nm.

Method 9 (LC-MS):

MS instrument: Waters SQD; HPLC instrument: Waters UPLC; column: Zorbax SB-Aq (Agilent), 50 mm×2.1 mm, 1.8 μm; mobile phase A: water+0.025% formic acid, mobile phase B: acetonitrile+0.025% formic acid; gradient: 0.0 min 98% A→0.9 min 25% A 1.0 min 5% A→1.4 min 5% A→1.41 min 98% A 1.5 min 98% A; oven: 40° C.; flow rate: 0.60 ml/min; UV detection: DAD, 210 nm.

Starting Materials and Intermediates

Example 1A rac-Methyl 4-{[(8-methoxy-1,2,3,4-tetrahydronaphthalen-2-yl)amino]methyl}benzoate

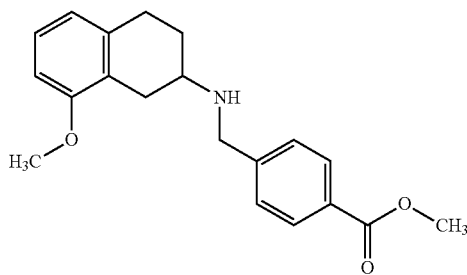 [SMILES: COC(=O)c1ccc(CNC2CCc3cccc(OC)c3C2)cc1]

15 g (74.4 mmol) of methyl 4-(aminomethyl)benzoate hydrochloride, 13.8 g (78.1 mmol) of 8-methoxy-3,4-dihydronaphthalen-2(1H)-one [for the preparation, see WO 2005/012291-A1, Example 45], 14.3 ml (81.8 mmol) of N,N-diisopropylethylamine, 4.7 ml of acetic acid and 20.5 g (96.7 mmol) of sodium triacetoxyborohydride were suspended in 600 ml of dichloromethane and stirred at RT overnight. The reaction mixture was then concentrated and the residue was stirred with ethyl acetate and water at RT for 1 h. The resulting precipitated solid was filtered off with suction. The filtrate phases were separated and the aqueous phase was extracted twice with ethyl acetate. The combined organic phases were dried and concentrated. The solid obtained above (18.2 g) and the residue of the organic phase (12.9 g) were combined and once more stirred in a mixture of dichloromethane, water and saturated potassium carbonate solution (pH 12) until everything had gone into solution. The organic phase was then separated off, dried and concentrated. The title compound was obtained in the form of the residue.

Yield: 20.4 g (83% of theory)

LC-MS (method 2): $R_t$=0.71 min; MS (ESIpos): m/z=326 $[M+H]^+$ $^1$H-NMR (400 MHz, DMSO-$d_6$): δ [ppm]=7.90 (d, 2H), 7.52 (d, 2H), 7.04 (t, 1H), 6.71 (d, 1H), 6.65 (d, 1H), 3.79-3.96 (m, 5H), 3.74 (s, 3H), 2.86-3.01 (m, 1H), 2.71-2.86 (m, 2H), 2.57-2.71 (m, 1H), 2.10-2.41 (m, 2H), 1.85-2.05 (m, 1H), 1.34-1.58 (m, 1H).

Example 2A rac-Methyl 4-{[(5-ethoxy-5-oxopentyl)(8-methoxy-1,2,3,4-tetrahydronaphthalen-2-yl)amino]methyl}benzoate

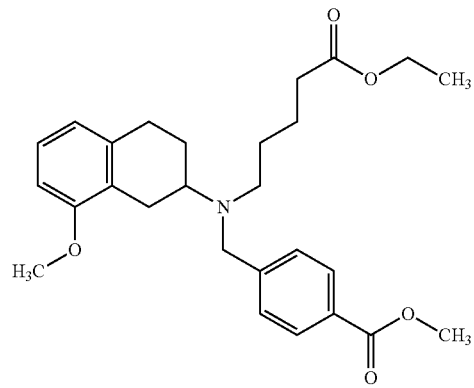 [SMILES: CCOC(=O)CCCCN(Cc1ccc(C(=O)OC)cc1)C1CCc2cccc(OC)c2C1]

Under argon, 13.4 g (41.2 mmol) of the compound from Example 1A were dissolved in 160 ml of acetonitrile, 11.8 ml (15.5 g, 74.1 mmol) of ethyl 5-bromovalerate, 27 g (82.4 mmol) of cesium carbonate and 685 mg (4.1 mmol) of potassium iodide were added and the mixture was stirred under reflux overnight. After addition of a further 550 mg of potassium iodide, the mixture was once more stirred under reflux overnight. Another 2 g of potassium iodide were then added, and the mixture was again stirred under reflux overnight. After cooling, the precipitate was filtered off and the filtrate was concentrated. This residue was then purified chromatographically on 1.2 kg of silica gel using the mobile phase isohexane/ethyl acetate (gradient 10:1→5:1). This gave 10.95 g (59% of theory) of the title compound as a colorless solid.

LC-MS (method 2): $R_t$=0.86 min; MS (ESIpos): m/z=454 $[M+H]^+$ $^1$H-NMR (400 MHz, DMSO-$d_6$): δ [ppm]=7.90 (d, J=8.07 Hz, 2H), 7.50 (d, J=8.07 Hz, 2H), 7.04 (t, J=7.83 Hz, 1H), 6.52-6.81 (m, 2H), 4.00 (q, J=7.09 Hz, 2H), 3.83 (s, 3H), 3.61-3.80 (m, 5H), 2.82 (d, J=15.41 Hz, 3H), 2.70 (br. s, 1H), 2.18 (t, J=7.21 Hz, 2H), 1.87-2.04 (m, 1H), 1.28-1.65 (m, 4H), 1.13 (t, J=7.09 Hz, 3H).

Example 3A rac-Methyl 4-{[(8-hydroxy-1,2,3,4-tetrahydronaphthalen-2-yl)(5-methoxy-5-oxopentyl)amino]methyl}benzoate

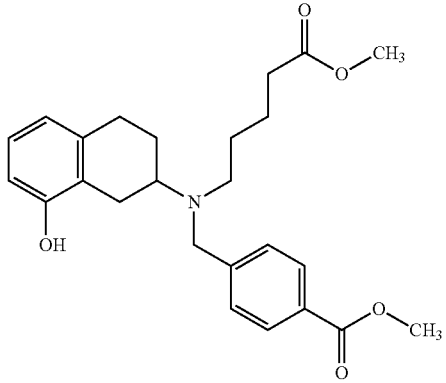 [SMILES: COC(=O)CCCCN(Cc1ccc(C(=O)OC)cc1)C1CCc2cccc(O)c2C1]

Under argon and at 0° C., 3 ml (3 mmol) of a 1N solution of boron tribromide in dichlormethane were added dropwise to a solution of 1.2 g (2.65 mmol) of the compound from Example 2A in 35 ml of dichloromethane, and the mixture was stirred at 0° C. for 1 h. A further 6 ml (6 mmol) of the boron tribromide solution were then added dropwise, and the mixture was stirred for another 45 min (at the end of the addition, a lightly colored precipitate was formed). 35 ml of methanol were then added dropwise, and the resulting solution was heated under reflux for 3 h and finally concentrated. The residue was dissolved in 80 ml of methanol, 0.2 ml of thionyl chloride was added and the mixture was heated under reflux for 4 h. The reaction was then concentrated again. What remained were 1.15 g of the title compound as a crude product which was reacted further in this form.

LC-MS (method 4): $R_t$=0.86 min; MS (ESIpos): m/z=426 [M+H]$^+$.

Pure material for the NMR spectroscopy was obtained by silica gel chromatography of a sample using a mobile phase gradient of dichloromethane and 0-12% methanol.

$^1$H-NMR (400 MHz, DMSO-d$_6$): δ [ppm]=9.18 (s, 1H), 7.85-7.96 (m, 2H), 7.51 (m, 2H), 6.85 (t, 1H), 6.56 (d, 1H), 6.48 (d, 1H), 3.83 (s, 3H), 3.73 (q, 2H), 3.54 (s, 3H), 2.60-2.93 (m, 4H), 2.30-2.45 (m, 2H), 2.20 (t, 2H), 1.88-1.97 (m, 1H), 1.28-1.75 (m, 6H).

Example 4A rac-Ethyl 4-{[(5-ethoxy-5-oxopentyl)(8-hydroxy-1,2,3,4-tetrahydronaphthalen-2-yl)amino]methyl}benzoate hydrochloride

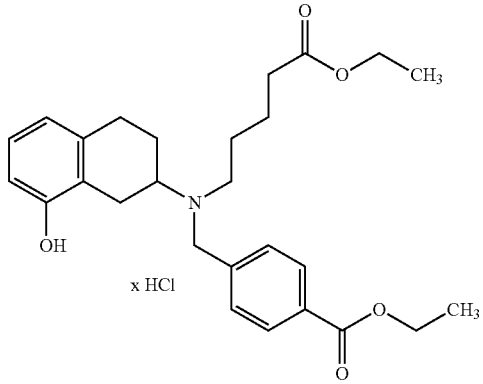 [SMILES: CCOC(=O)CCCCN(Cc1ccc(C(=O)OCC)cc1)C1CCc2cccc(O)c2C1]

8.8 g (20.7 mmol) of the compound from Example 3A were dissolved in 270 ml of THF and 130 ml of methanol and, after addition of 25.5 ml of 5 N aqueous sodium hydroxide solution, stirred at RT overnight. The mixture was then acidified with 27 ml of 5 N hydrochloric acid and concentrated under reduced pressure, and the residue was dried further under high vacuum. The residue (15.7 g which, according to LC-MS, still contain starting material) was dissolved in ethanol, another 25.5 ml of 5 N aqueous sodium hydroxide solution were added and the mixture was stirred under reflux for 1 h. The mixture was then concentrated again, and the residue was co-distilled twice with ethanol. According to LC-MS (method 2), 79% of the residue that remained consisted of the dicarboxylic acid 4-{[(4-carboxybutyl)(8-hydroxy-1,2,3,4-tetrahydronaphthalen-2-yl)amino]methyl}benzoic acid ($R_t$=0.61 min; MS (ESIpos): m/z=398 [M+H]$^+$).

This residue was partially dissolved in 210 ml of ethanol, 1.9 ml of thionyl chloride were added dropwise and the mixture was stirred at 65° C. for 6 h. The mixture was diluted with further ethanol until the reaction became stirrable once more, and the mixture was stirred at 65° C. for another 6 h. After addition of a further 10 ml of thionyl chloride, the mixture was once more stirred at 65° C. overnight. After cooling, inorganic material was filtered off with suction and the residue was washed with ethanol. About 100 ml of ethanol were added to the concentrated filtrate (about 17 g), and the mixture was shaken vigorously and then once more filtered off with suction. The solid was washed with about 50 ml of ethanol and dried at 40° C. under reduced pressure.

Yield: 4.3 g of a brownish solid

LC-MS (method 2): $R_t$=0.86 min; MS (ESIpos): m/z=454 [M+H]$^+$ $^1$H-NMR (400 MHz, DMSO-d$_6$): δ [ppm]=10.32-10.57 (br, 1H), 9.52-9.65 (m, 1H), 7.98-8.09 (m, 2H), 7.76-7.93 (m, 2H), 6.88-7.01 (m, 1H), 6.60-6.71 (m, 1H), 6.48-6.61 (m, 1H), 4.22-4.77 (m, 4H), 3.94-4.09 (m, 2H), 3.49-3.73 (m, 1H), 2.95-3.28 (m, 3H), 2.60-2.93 (m, 3H), 2.14-2.45 (m, 3H), 1.38-2.00 (m, 6H), 1.25-1.38 (m, 3H), 1.08-1.20 (m, 3H).

Example 5A rac-Methyl 4-{[{8-[(4-tert-butylbenzyl)oxy]-1,2,3,4-tetrahydronaphthalen-2-yl}(5-methoxy-5-oxo-pentyl)amino]methyl}benzoate

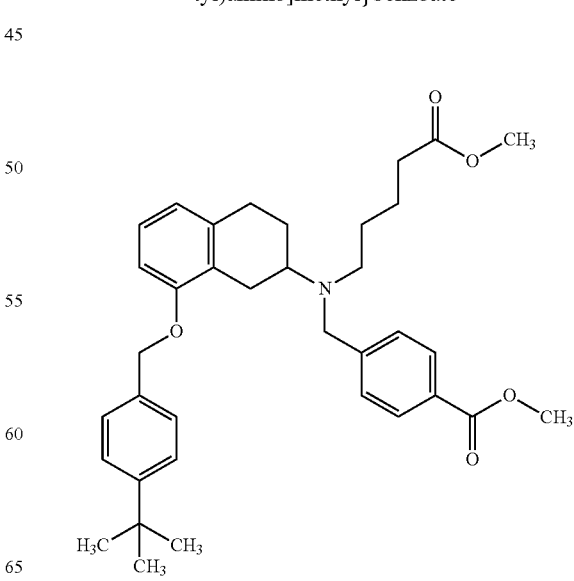

550 mg (1.29 mmol) of the compound from Example 3A were dissolved in 35 ml of DMF, 320 μl (1.6 mmol) of 4-tert-butylbenzyl bromide and 1.4 g (4.14 mmol) of cesium carbonate were added and the mixture was stirred at RT for 18 h. Water was then added, and the mixture was extracted repeatedly with ethyl acetate. The combined organic phases were dried over sodium sulfate and concentrated. The crude product obtained was purified by preparative HPLC (method 1).

Yield: 230 mg (31% of theory)

LC-MS (method 3): $R_t$=2.32 min; MS (ESIpos): m/z=572 [M+H]$^+$.

Example 6A and Example 7A ent-Methyl 4-{[{8-[(4-tert-butylbenzyl)oxy]-1,2,3,4-tetrahydronaphthalen-2-yl}(5-methoxy-5-oxo-pentyl)amino]methyl}benzoate (enantiomer 1 and 2)

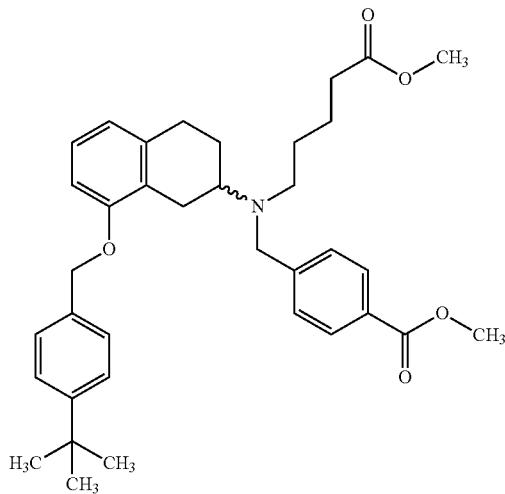 [SMILES: COC(=O)CCCCN(Cc1ccc(C(=O)OC)cc1)C1CCc2cccc(OCc3ccc(C(C)(C)C)cc3)c2C1]

160 mg of the racemic methyl 4-{[{8-[(4-tert-butylbenzyl)oxy]-1,2,3,4-tetrahydronaphthalen-2-yl}(5-methoxy-5-oxo-pentyl)amino]methyl}benzoate from Example 5A were separated into the enantiomers by preparativer HPLC on a chiral phase [sample preparation: the substance was dissolved in 10 ml of isopropanol and 10 ml of hexane were added to the solution; injection volume: in each case 1 ml; column: Daicel Chiralpak OD-H, 250 mm×20 mm; mobile phase: isohexane/isopropanol 80:20 (v/v); flow rate: 18 ml/min; UV detection: 230 nm; temperature: RT]:

Example 6A (Enantiomer 1)

Yield: 34 mg

LC-MS (method 4): $R_t$=1.43 min; MS (ESIpos): m/z=572 [M+H]$^+$

HPLC (method 5): $R_t$=5.28 min, 99.5% ee $^1$H-NMR (400 MHz, DMSO-d$_6$): δ [ppm]=7.83-7.98 (m, 2H), 7.27-7.57 (m, 6H), 6.95-7.07 (m, 1H), 6.74-6.84 (m, 1H), 6.58-6.70 (m, 1H), 5.05 (s, 2H), 3.65-3.83 (m, 5H), 3.53 (s, 3H), 2.61-2.99 (m, 4H), 2.14-2.26 (m, 2H), 1.87-2.05 (m, 1H), 1.45-1.65 (m, 3H), 1.34-1.44 (m, 2H), 1.29 (s, 9H).

Example 7A (Enantiomer 2)

Yield: 31 mg

LC-MS (method 4): $R_t$=1.43 min; MS (ESIpos): m/z=572 [M+H]$^+$

HPLC (method 5): $R_t$=6.02 min, 96.7% ee.

Analogously to the procedure for Example 5A, the following compounds were prepared from rac-methyl 4-{[(8-hydroxy-1,2,3,4-tetrahydronaphthalen-2-yl)(5-methoxy-5-oxopentyl)amino]-methyl}benzoate and the respective alkyl halide listed:

| Example | Structure | Starting material | Yield; analytical data |
|---|---|---|---|
| 8A | (racemate) | 1-(chloromethyl)-4-(2-phenylethyl)-benzene | 14% of theory; LC-MS (method 2): $R_t$ = 1.22 min, m/z = 620 [M + H]$^+$ |

| Example | Structure | Starting material | Yield; analytical data |
|---|---|---|---|
| 9A | 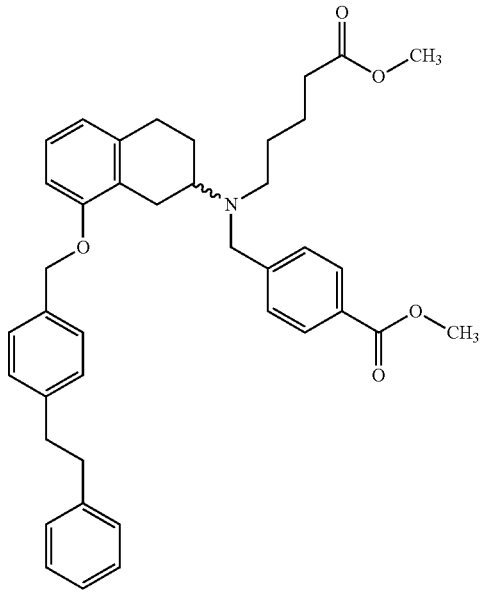<br>(enantiomer 1) | Example 8A[1)] | 34% of theory;<br>LC-MS (method 2):<br>$R_t$ = 1.19 min,<br>m/z = 620 [M + H]$^+$;<br>HPLC (method 6):<br>$R_t$ = 4.56 min,<br>>99.5% ee |
| 10A | 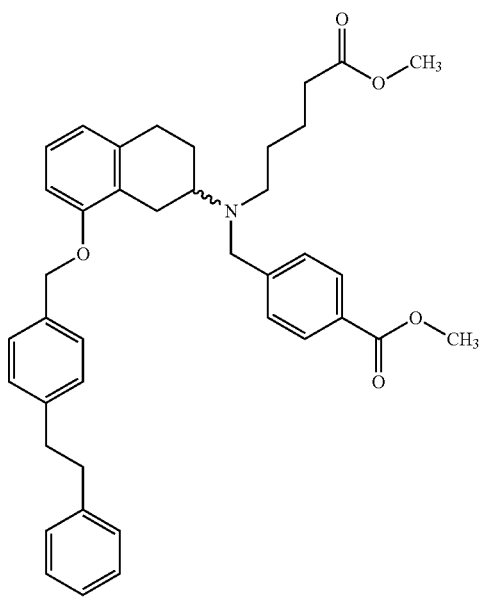<br>(enantiomer 2) | Example 8A[1)] | 35% of theory;<br>LC-MS (method 2):<br>$R_t$ = 1.18 min,<br>m/z = 620 [M + H]$^+$;<br>HPLC (method 6):<br>$R_t$ = 5.26 min,<br>96.8% ee |

-continued

| Example | Structure | Starting material | Yield; analytical data |
|---|---|---|---|
| 11A | (racemate) | 1-(3-chloro-propyl)-pyrrolidin-2-one | 10% of theory; LC-MS (method 2): $R_t$ = 0.79 min, m/z = 551 [M + H]$^+$ |
| 12A | (racemate) | 3-(3-chloro-propyl)-1,3-oxazolidin-2-one | 55% of theory; LC-MS (method 4): $R_t$ = 0.93 min, m/z = 553 [M + H]$^+$ |
| 13A | (racemate) | 4-(3-bromo-propyl)-morpholin-3-one | 14% of theory; LC-MS (method 2): $R_t$ = 0.84 min, m/z = 567 [M + H]$^+$ |

[1]Method for the separation of enantiomers:

Sample preparation: 100 mg of the racemate were dissolved in 10 ml of isopropanol, and 10 ml of hexane were added to the solution; injection volume: in each case 0.1 ml; column: Daicel Chiralpak IA, 250 mm x 20 mm; mobile phase: ethanol/methyl tert-butyl ether 75:25 (v/v); flow rate: 18 ml/min; UV detection: 230 nm; temperature: RT.

Working Examples

Example 1 rac-4-{[{8-[(4-tert-Butylbenzyl)oxy]-1,2,3,4-tetrahydronaphthalen-2-yl}(4-carboxybutyl)amino]-methyl}benzoic acid

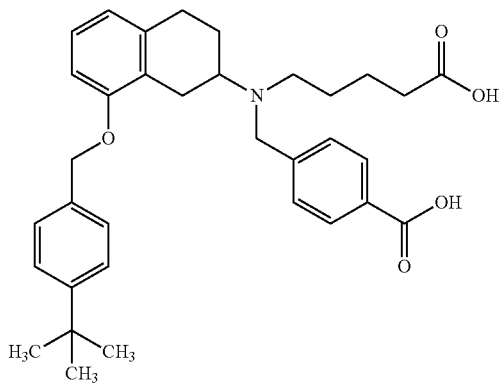 [SMILES: CC(C)(C)c1ccc(COc2cccc3c2CC(N(CCCCC(=O)O)Cc2ccc(C(=O)O)cc2)CC3)cc1]

68.5 mg (0.12 mmol) of the compound from Example 5A were dissolved in 0.5 ml of methanol and 1 ml of dioxane, 0.15 ml of 45% strength aqueous sodium hydroxide solution and 0.2 ml of water were added and the mixture was then stirred at a bath temperature of 100° C. for 45 min. The milky suspension was then diluted with water, acidified with 2 N hydrochloric acid and extracted repeatedly with dichloromethane. The combined organic phases were dried over sodium sulfate and concentrated. The residue was purified by preparative HPLC (method 1).

Yield: 50.5 mg (76% of theory)

LC-MS (method 2): $R_t$=1.01 min; MS (ESIpos): m/z=544 $[M+H]^+$ $^1$H-NMR (500 MHz, DMSO-$d_6$): δ [ppm]=7.92 (d, 2H), 7.28-7.63 (m, 6H), 7.04 (t, 1H), 6.82 (d, 1H), 6.68 (d, 1H), 4.95-5.20 (m, 2H), 5.08 (s, 2H), 3.69-3.92 (m, 2H), 2.65-3.01 (m, 4H), 2.18 (br. s, 2H), 1.87-2.08 (m, 1H), 1.39-1.70 (m, 5H), 1.32 (s, 9H).

The following compounds were prepared analogously to the procedure for Example 1:

| Example | Structure | Starting material | Yield; analytical data |
|---|---|---|---|
| 2 | (enantiomer 1) | 6A | 73% of theory; LC-MS (method 2): $R_t$ = 1.01 min, m/z = 544 [M + H]$^+$ |

| Example | Structure | Starting material | Yield; analytical data |
|---|---|---|---|
| 3 | 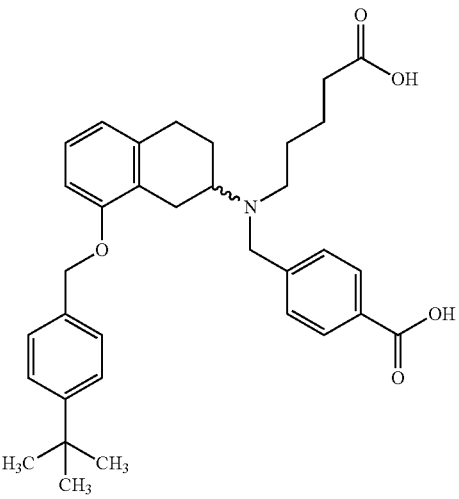<br>(enantiomer 2) | 7A | 28% of theory;<br>LC-MS (method 2):<br>$R_t = 1.02$ min,<br>m/z = 544 $[M + H]^+$ |
| 4 | 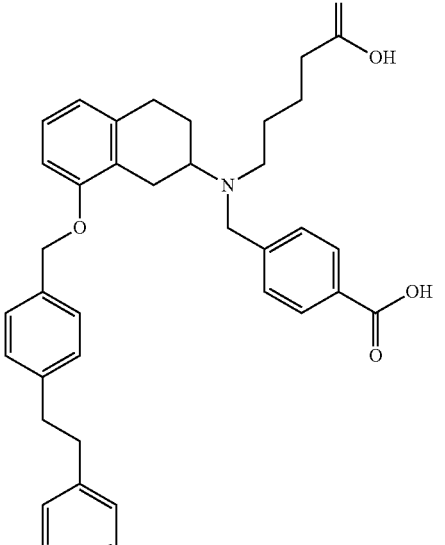<br>(racemate) | 8A[1)] | 87% of theory;<br>LC-MS (method 4):<br>$R_t = 1.27$ min,<br>m/z = 592 $[M + H]^+$ |

| Example | Structure | Starting material | Yield; analytical data |
|---|---|---|---|
| 5 | 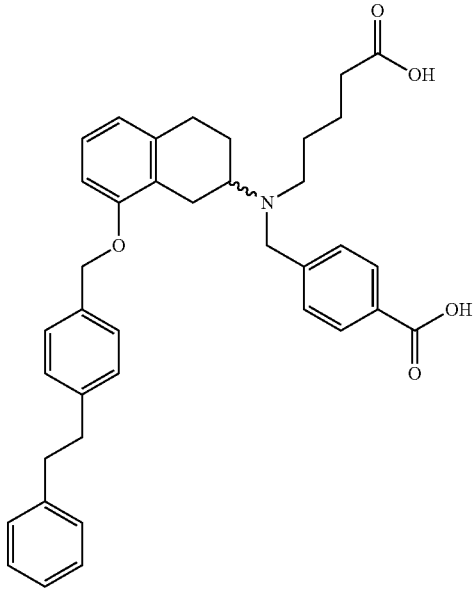<br>(enantiomer 1) | 9A | 72% of theory;<br>LC-MS (method 2):<br>$R_t = 1.05$ min,<br>m/z = 592 $[M + H]^+$;<br>HPLC (method 6):<br>$R_t = 4.56$ min,<br>>99.5% ee |
| 6 | 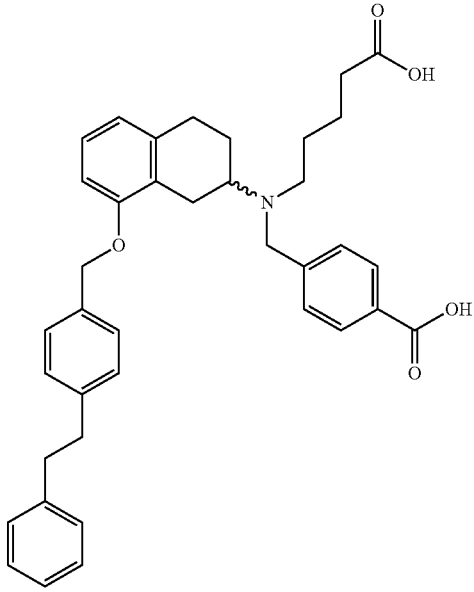<br>(enantiomer 2) | 10A | 68% of theory;<br>LC-MS (method 2):<br>$R_t = 1.05$ min,<br>m/z = 592 $[M + H]^+$;<br>HPLC (method 6):<br>$R_t = 5.26$ min,<br>96.8% ee<br>$^1$H-NMR (400 MHz, DMSO-$d_6$): δ [ppm] = 7.88 (d, 2H), 7.48 (d, 2H), 7.12-7.37 (m, 9H), 6.93-7.06 (m, 1H), 6.78 (d, 1H), 6.65 (d, 1H), 5.05 (s, 2H), 3.74 (dd, 2H), 2.62-2.95 (m, 8H), 2.15 (t, 2H), 1.99 (m, 1H), 1.31-1.68 (m, 5H). |

-continued

| Example | Structure | Starting material | Yield; analytical data |
|---|---|---|---|
| 7 | (racemate) | 11A[1)3)] | 84% of theory; LC-MS (method 2): $R_t = 0.75$ min, m/z = 523 $[M + H]^+$ |
| 8 | (racemate) | 12A[2)] | 21% of theory; LC-MS (method 2): $R_t = 0.72$ min, m/z = 525 $[M + H]^+$ |
| 9 | (racemate) | 13A[1)4)] | 79% of theory; LC-MS (method 2): $R_t = 0.72$ min, m/z = 539 $[M + H]^+$ |

[1)]Here, for work-up, dilute formic acid was added to the reaction mixture and the product was purified directly by preparative HPLC.
[2)]The ester hydrolysis was carried out at a bath temperature of 50° C.
[3)]The ester hydrolysis was carried out at a bath temperature of 70° C.
[4)]The ester hydrolysis was carried out at room temperature.

General Procedure for Preparing Further Working Examples by Means Pf Parallel Synthesis:

In each case 1.2 equivalents (0.12 mmol) of the alkyl halide in question were initially charged in a well of a 96-well deep well microtiter plate, and a solution of 47 mg (0.1 mmol) of the compound from Example 4A in 0.6 ml of DMF was added. 44 mg (0.32 mmol) of potassium carbonate were added to this mixture. The microtiter plate was covered and shaken at 80° C. overnight. The mixture was then filtered, 0.6 ml of 4 N aqueous sodium hydroxide solution was added to the filtrate and the plate was covered again and shaken at 60° C. overnight. The solvent was then evaporated. The residue was taken up in 0.6 ml of DMSO and purified directly by preparative LC-MS (method 7 or 8). The product-containing fractions were concentrated under reduced pressure using a centrifugal dryer. The residues of the individual fractions were dissolved in in each case 0.6 ml of DMSO and combined. The solvent was then evaporated completely in the centrifugal dryer.

Using this procedure, the following compounds were obtained:
| Example | Structure | LC-MS (Method 9) |
|---|---|---|
| 10 | 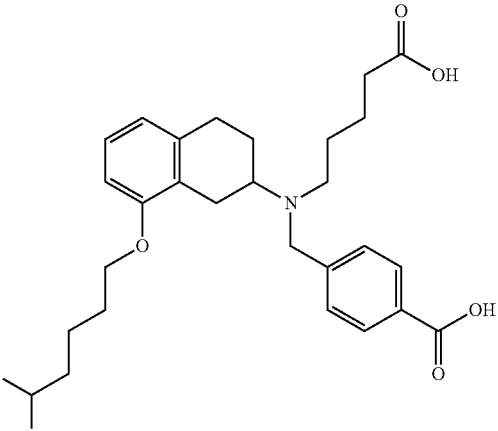<br>(racemate) | $R_t$ = 1.01 min,<br>m/z = 496 [M + H]$^+$ |
| 11 | 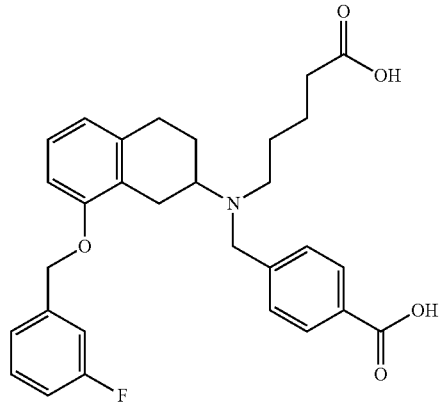<br>(racemate) | $R_t$ = 0.93 min,<br>m/z = 506 [M + H]$^+$ |
| 12 | 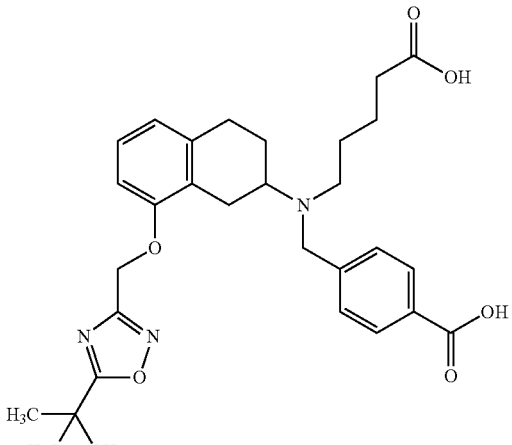<br>(racemate) | $R_t$ = 0.90 min,<br>m/z = 536 [M + H]$^+$ |

-continued

| Example | Structure | LC-MS (Method 9) |
|---|---|---|
| 13 | (racemate) | R$_t$ = 0.95 min, m/z = 468 [M + H]$^+$ |
| 14 | (racemate) | R$_t$ = 0.92 min, m/z = 486 [M + H]$^+$ |
| 15 | (racemate) | R$_t$ = 0.93 min, m/z = 502 [M + H]$^+$ |

| Example | Structure | LC-MS (Method 9) |
|---|---|---|
| 16 | 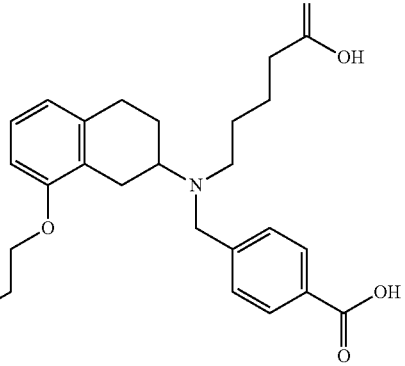<br>(racemate) | $R_t$ = 0.85 min,<br>m/z = 479 [M + H]$^+$ |
| 17 | 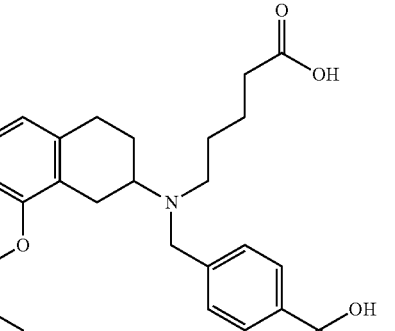<br>(racemate) | $R_t$ = 0.80 min,<br>m/z = 489 [M + H]$^+$ |

B. ASSESSMENT OF THE PHARMACOLOGICAL ACTIVITY

The pharmacological effect of the compounds according to the invention can be shown in the following assays:

B-1. Action at a Recombinant Guanylate Cyclase Reporter Cell Line

The cellular action of the compounds according to the invention is determined at a recombinant guanylate cyclase reporter cell line, as described in F. Wunder et al., *Anal. Biochem.* 339, 104-112 (2005).

Representative results for the compounds according to the invention are listed in Table 1:

TABLE 1 sGC-activating activity in the CHO reporter cell in vitro

| Example No. | MEC [nM] |
|---|---|
| 1 | 0.3 |
| 4 | 3.0 |
| 5 | 0.3 |
| 10 | 30 |
| 11 | 300 |

(MEC = minimum effective concentration).

B-2. Stimulation of sGC Enzyme Activity

Soluble guanylate cyclase (sGC) converts on stimulation GTP into cGMP and pyrophosphate (PPi). PPi is detected with the aid of the assay described below. The signal produced in the assay increases as the reaction progresses and serves as a measure of the sGC enzyme activity under the given stimulation.

To carry out the assay, 29 µl of enzyme solution [0-10 nM soluble guanylate cyclase (prepared according to Honicka et al., *J. Mol. Med.* 77, 14-23 (1999)) in 50 mM TEA, 2 mM MgCl$_2$, 0.1% BSA (fraction V), 0.005% Brij®, pH 7.5] are initially introduced into a microplate, and 1 µl of the substance to be tested (as a serially diluted solution in DMSO) is added. The mixture is incubated at room temperature for 10 min. Then 20 µl of detection mix [1.2 nM Firefly Luciferase (*Photinus pyralis* luciferase, Promega), 29 µM dehydroluciferin (prepared according to Bitler & McElroy, *Arch. Biochem. Biophys.* 72, 358 (1957)), 122 µM luciferin (Promega), 153 µM ATP (Sigma) and 0.4 mM DTT (Sigma) in 50 mM TEA, 2 mM MgCl$_2$, 0.1% BSA (fraction V), 0.005% Brij®, pH 7.5] are added. The enzyme reaction is started by adding 20 µl of substrate solution [1.25 mM guanosine 5'-triphosphate (Sigma) in 50 mM TEA, 2 mM MgCl$_2$, 0.1% BSA (fraction V), 0.005% Brij®, pH 7.5] and measured continuously in a luminometer. The extent of the stimulation by the substance to be tested can be determined relative to the signal of the unstimulated reaction.

The activation of heme-free guanylate cyclase is examined by addition of 25 μM of 1H-1,2,4-oxadiazolo[4,3-a]quinoxalin-1-one (ODQ) to the enzyme solution and subsequent incubation for 30 minutes and compared to the stimulation of the native enzyme.

Representative results for the compounds according to the invention are listed in Table 2:

TABLE 2

Activating action at the sGC enzyme in vitro

| Example No. | MEC [nM] | EC$_{50}$ [nM] |
|---|---|---|
| 1 | 0.12 | 8.5 |
| 4 | 0.7 | 7.5 |
| 5 | 0.13 | 1.4 |
| 7 | 830 | |
| 9 | 700 | |
| 10 | 48 | 620 |
| 11 | 200 | |
| 12 | 205 | |

(MEC = minimum effective concentration; EC$_{50}$ = concentration at 50% of maximum efficacy).

B-3. Vasorelaxant Effect In Vitro:

Rabbits are anesthetized and sacrificed by intravenous injection of thiopental sodium (about 50 mg/kg) and exsanguinated. The saphenous artery is removed and divided into rings 3 mm wide. The rings are mounted singly on in each case a pair of triangular hooks open at the end and made of 0.3 mm-thick special wire (Remanium®). Each ring is placed under an initial tension in 5 ml organ baths with Krebs-Henseleit solution which is at 37° C., is gassed with carbogen and has the following composition: NaCl 119 mM; KCl 4.8 mM; CaCl$_2$×2 H$_2$O 1 mM; MgSO$_4$×7 H$_2$O 1.4 mM; KH$_2$PO$_4$ 1.2 mM; NaHCO$_3$ 25 mM; glucose 10 mM; bovine serum albumin 0.001%. The force of contraction is detected with Statham UC2 cells, amplified and digitized via A/D converters (DAS-1802 HC, Keithley Instruments, Munich) and recorded in parallel on chart recorders. Contractions are induced by addition of phenylephrine.

After several (generally 4) control cycles, the substance to be investigated is added in each further run in increasing dosage, and the level of the contraction achieved under the influence of the test substance is compared with the level of the contraction reached in the last preceding run. The concentration necessary to reduce the contraction reached in the preceding control by 50% is calculated from this (IC$_{50}$). The standard application volume is 5 μl. The proportion of DMSO in the bath solution corresponds to 0.1%.

Representative results for the compounds according to the invention are listed in Table 3:

TABLE 3

Vasorelaxant effect in vitro

| Example No. | IC$_{50}$ [nM] |
|---|---|
| 1 | 113 |
| 5 | 9140 |
| 6 | 4380 |

B-4. Radiotelemetric Measurement of Blood Pressure and Heart Rate on Conscious SH Rats A commercially available telemetry system from Data Sciences International DSI, USA, is employed for the measurements on conscious SH rats described below.

The system consists of 3 main components: (1) implantable transmitters, (2) receivers, which are linked via a multiplexer to a (3) data acquisition computer. The telemetry system makes it possible to continuously record the blood pressure and heart rate of conscious animals in their usual habitat.

The investigations are carried out on adult female spontaneously hypertensive rats (SH rats) with a body weight of >200 g. After transmitter implantation, the experimental animals are housed singly in type 3 Makrolon cages. They have free access to standard feed and water. The day/night rhythm in the experimental laboratory is changed by the room lighting at 6.00 am and at 7.00 pm.

The telemetry transmitters (TAM PA-C40, DSI) employed are surgically implanted under aseptic conditions in the experimental animals at least 14 days before the first experimental use. The animals instrumented in this way can be employed repeatedly after the wound has healed and the implant has settled.

For the implantation, the fasted animals are anesthetized with pentobarbital (Nembutal, Sanofi, 50 mg/kg i.p.) and shaved and disinfected over a large area of their abdomens. After the abdominal cavity has been opened along the linea alba, the liquid-filled measuring catheter of the system is inserted into the descending aorta in the cranial direction above the bifurcation and fixed with tissue glue (VetBonD™, 3M). The transmitter housing is fixed intraperitoneally to the abdominal wall muscle, and layered closure of the wound is performed. An antibiotic (Tardomyocel COMP, Bayer AG, 1 ml/kg s.c.) is administered postoperatively for prophylaxis of infection.

Outline of Experiment:

The substances to be investigated are administered orally by gavage in each case to a group of animals (n=6). The test substances are dissolved in suitable solvent mixtures, or suspended in 0.5% strength Tylose, appropriate for an administration volume of 5 ml/kg of body weight. A solvent-treated group of animals is employed as control.

The telemetry measuring unit is configured for 24 animals. Each experiment is recorded under an experiment number.

Each of the instrumented rats living in the system is assigned a separate receiving antenna (1010 Receiver, DSI). The implanted transmitters can be activated externally by means of an incorporated magnetic switch and are switched to transmission in the run-up to the experiment. The emitted signals can be detected online by a data acquisition system (Dataquest™ A.R.T. for Windows, DSI) and be appropriately processed. The data are stored in each case in a file created for this purpose and bearing the experiment number.

In the standard procedure, the following are measured for 10-second periods in each case: (1) systolic blood pressure (SBP), (2) diastolic blood pressure (DBP), (3) mean arterial pressure (MAP) and (4) heart rate (HR).

The acquisition of measured values is repeated under computer control at 5-minute intervals. The source data obtained as absolute value are corrected in the diagram with the currently measured barometric pressure and stored as individual data. Further technical details are given in the documentation from the manufacturing company (DSI).

The test substances are administered at 9.00 am on the day of the experiment. Following the administration, the parameters described above are measured over 24 hours. After the end of the experiment, the acquired individual data are sorted using the analysis software (Dataquest™ A.R.T. Analysis). The void value is assumed to be the time 2 hours before administration of the substance, so that the selected data set includes the period from 7.00 am on the day of the experiment to 9.00 am on the following day.

The data are smoothed over a presettable time by determination of the average (15-minute average, 30-minute average) and transferred as a text file to a storage medium. The measured values presorted and compressed in this way are transferred into Excel templates and tabulated.

C. EXEMPLARY EMBODIMENTS OF PHARMACEUTICAL COMPOSITIONS

The compounds according to the invention can be converted into pharmaceutical preparations in the following ways:

Tablet:

Composition:

100 mg of the compound according to the invention, 50 mg of lactose (monohydrate), 50 mg of maize starch (native), 10 mg of polyvinylpyrrolidone (PVP 25) (from BASF, Ludwigshafen, Germany) and 2 mg of magnesium stearate.

Tablet weight 212 mg, diameter 8 mm, radius of curvature 12 mm.

Production:

The mixture of compound according to the invention, lactose and starch is granulated with a 5% strength solution (m/m) of the PVP in water. The granules are dried and then mixed with the magnesium stearate for 5 minutes. This mixture is compressed in a conventional tablet press (see above for format of the tablet). A guideline compressive force for the compression is 15 kN.

Suspension which can be Administered Orally:

Composition:

1000 mg of the compound according to the invention, 1000 mg of ethanol (96%), 400 mg of Rhodigel® (xanthan gum from FMC, Pennsylvania, USA) and 99 g of water.

10 ml of oral suspension correspond to a single dose of 100 mg of the compound according to the invention.

Production:

The Rhodigel is suspended in ethanol, and the compound according to the invention is added to the suspension. The water is added while stirring. The mixture is stirred for about 6 h until the swelling of the Rhodigel is complete.

Solution which can be Administered Orally:

Composition:

500 mg of the compound according to the invention, 2.5 g of polysorbate and 97 g of polyethylene glycol 400.20 g of oral solution correspond to a single dose of 100 mg of the compound according to the invention.

Production:

The compound according to the invention is suspended in the mixture of polyethylene glycol and polysorbate with stirring. The stirring process is continued until the compound according to the invention has completely dissolved.

i.v. Solution:

The compound according to the invention is dissolved in a concentration below the saturation solubility in a physiologically tolerated solvent (e.g. isotonic saline, 5% glucose solution and/or 30% PEG 400 solution). The solution is sterilized by filtration and used to fill sterile and pyrogen-free injection containers.

The invention claimed is:

1. A compound of the formula (I)

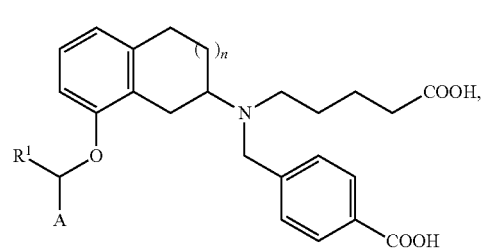

in which
n represents the number 0, 1 or 2,
$R^1$ represents hydrogen or methyl
and
A represents a group of the formula

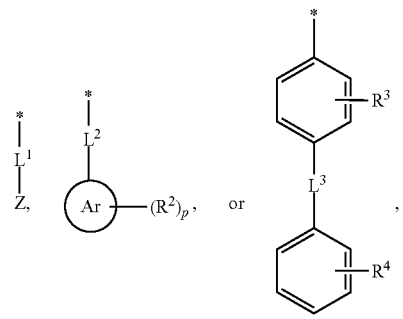

in which
* denotes the respective point of attachment to the remainder of the molecule,
$L^1$ represents straight-chain $(C_1-C_5)$-alkanediyl which may be mono- or disubstituted by methyl and mono- or disubstituted by fluorine,
Z represents hydrogen, fluorine, cyano, trifluoromethyl or a group of the formula

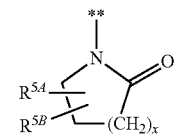

in which
** denotes the point of attachment to group $L^1$,
x represents the number 1, 2 or 3, where one of these $CH_2$ groups may be replaced by —O—,
and
$R^{5A}$ and $R^{5B}$ independently of one another represent hydrogen or methyl,
$L^2$ represents a bond or straight-chain $(C_1-C_5)$-alkanediyl,
Ar represents phenyl or 5- or 6-membered heteroaryl having up to three ring heteroatoms from the group consisting of N, O and S,
$R^2$ represents a substituent selected from the group consisting of fluorine, chlorine, bromine, cyano, $(C_1-C_4)$-alkyl, trifluoromethyl, $(C_1-C_4)$-alkoxy and trifluoromethoxy, p represents the number 0, 1 or 2, where, if the substituent $R^2$ occurs twice, its individual meanings may be identical or different, $L^3$ represents a bond, —O—, —CH$_2$—, —CH$_2$—CH$_2$— or —CH=CH— and $R^3$ and $R^4$ independently of one another represent hydrogen or a substituent selected from the group consisting of fluorine, chlorine, bromine, cyano, (C$_1$-C$_4$)-alkyl, trifluoromethyl, (C$_1$-C$_4$)-alkoxy and trifluoromethoxy, or a salt thereof.

2. The compound of claim 1 in which n represents the number 1, $R^1$ represents hydrogen and A represents a group of the formula

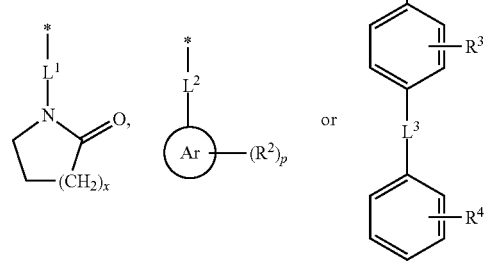

in which

* denotes the respective point of attachment to the remainder of the molecule, $L^1$ represents straight-chain (C$_2$-C$_4$)-alkanediyl, x represents the number 1 or 2, where one of these CH$_2$ groups may be replaced by —O—, $L^2$ represents a bond or —CH$_2$—, Ar represents phenyl, pyridyl, 1,2,4-oxadiazolyl or 1,3,4-oxadiazolyl, $R^2$ represents a substituent selected from the group consisting of fluorine, chlorine, (C$_1$-C$_4$)-alkyl and trifluoromethyl, p represents the number 0 or 1, $L^3$ represents a bond or —CH$_2$—CH$_2$— and $R^3$ and $R^4$ independently of one another represent hydrogen or a substituent selected from the group consisting of fluoroine, chlorine, (C$_1$-C$_4$)-alkyl and trifluoromethyl, or a salt thereof.

3. The compound of claim 1 in which n represents the number 1, $R^1$ represents hydrogen and A represents a group of the formula

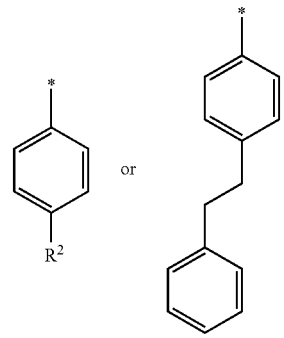

in which

* denotes the respective point of attachment to the remainder of the molecule and $R^2$ represents methyl, ethyl, isopropyl or tert-butyl, or a salt thereof.

4. A process for preparing a compound of the formula (I) as defined in claim 1, comprising:

reacting a compound of the formula (II)

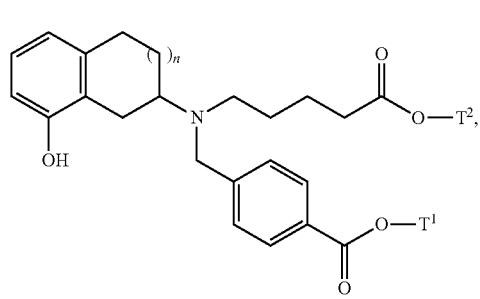

(II)

in which n has the meaning given in claim 1 and $T^1$ and $T^2$ are identical or different and represent (C$_1$-C$_4$)-alkyl, in the presence of a base with a compound of the formula (III)

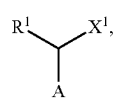

(III)

in which $R^1$ and A have the meanings given in claim 1 and $X^1$ represents a leaving group, to give a compound of the formula (IV)

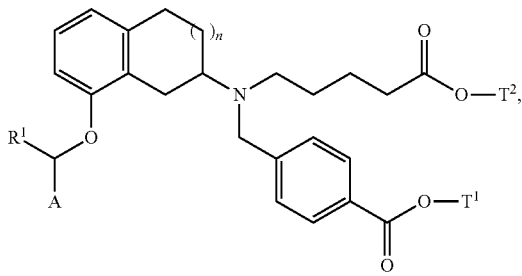

(IV)

in which n, $R^1$, A, $T^1$ and $T^2$ each have the meanings given above, and hydrolyzing the ester groupings —C(O)O$T^1$ and —C(O)O$T^2$ of the compound of formula (IV) into the corresponding dicarboxylic acid substituents of the compound of formula (I)

and optionally separating the compounds of the formula (I) into their enantiomers and/or diastereomers, and optionally reacting the compound of formula (I) with the appropriate (i) solvents and/or (ii) base or acid to give a solvate or salt thereof or a solvate of a salt thereof.

5. A pharmaceutical composition comprising a compound of claim 1 in combination with one or more inert, non-toxic, pharmaceutically suitable excipients.

6. The pharmaceutical composition of claim 5, further comprising at least one active ingredient selected from the group consisting of an organic nitrate, nitric oxide donor, a cyclic guanosine monophosphate-phosphodiesterase inhibitor, a stimulator of guanylate cyclase, an agent having antithrombotic activity, an agent lowering blood pressure, and an agent altering lipid metabolism.

7. A method for the treatment of heart failure, angina pectoris, hypertension, pulmonary hypertension, ischemias, thromboembolic disorders and arteriosclerosis comprising administering and effective amount of a compound of claim 1 to a human or animal in need thereof.

* * * * *